(12) United States Patent
Rajan et al.

(10) Patent No.: US 10,420,491 B2
(45) Date of Patent: Sep. 24, 2019

(54) DEVICE AND METHOD FOR GENERATING CALIBRATION FACTORS FOR USE IN DETERMINING BIOLOGICAL INDICATOR LEVELS IN TISSUE

(71) Applicant: LVL Technologies, Inc., Austin, TX (US)

(72) Inventors: Nithin O. Rajan, Austin, TX (US); Dustin M. Freckleton, Austin, TX (US); Paulo E. Xavier da Silveira, Boulder, CO (US); Byron Olson, Boone, IA (US)

(73) Assignee: LVL Technologies, Inc., Austin, TX (US)

( * ) Notice: Subject to any disclaimer, the term of this patent is extended or adjusted under 35 U.S.C. 154(b) by 0 days.

(21) Appl. No.: 15/576,671

(22) PCT Filed: May 26, 2016

(86) PCT No.: PCT/US2016/034403
§ 371 (c)(1),
(2) Date: Nov. 22, 2017

(87) PCT Pub. No.: WO2016/191588
PCT Pub. Date: Dec. 1, 2016

(65) Prior Publication Data
US 2018/0132767 A1    May 17, 2018

Related U.S. Application Data

(60) Provisional application No. 62/166,571, filed on May 26, 2015.

(51) Int. Cl.
*A61B 5/145* (2006.01)
*A61B 5/1455* (2006.01)
(Continued)

(52) U.S. Cl.
CPC ........ *A61B 5/14551* (2013.01); *A61B 5/0075* (2013.01); *A61B 5/0205* (2013.01);
(Continued)

(58) Field of Classification Search
CPC .................................................. A61B 5/14551
See application file for complete search history.

(56) References Cited

U.S. PATENT DOCUMENTS

| | | | |
|---|---|---|---|
| 4,981,355 A | | 1/1991 | Higgins |
| 5,259,381 A | * | 11/1993 | Cheung .............. A61B 5/02427 356/41 |
| 5,278,627 A | * | 1/1994 | Aoyagi .............. A61B 5/02427 250/252.1 |
| 5,356,593 A | | 10/1994 | Heiberger et al. |
| 5,910,109 A | | 6/1999 | Peters et al. |
| 6,651,015 B2 | * | 11/2003 | Samsoondar ........... G01J 3/433 702/28 |

(Continued)

FOREIGN PATENT DOCUMENTS

| | | |
|---|---|---|
| CA | 2879913 A1 | 1/2014 |
| WO | 2009079629 A2 | 6/2009 |
| WO | 2016191588 A1 | 12/2016 |

OTHER PUBLICATIONS

International Search Report and Written Opinion dated Sep. 2, 2016 for corresponding PCT Application No. PCT/US2016/034403.

*Primary Examiner* — Yara B Green
(74) *Attorney, Agent, or Firm* — Polsinelli PC

(57) ABSTRACT

Optical-electronic device configured to generate a calibration factor for use in determining optical density. The device includes at least one emitter configured to emit light, a detector configured to receive light and transmit data representative of the received light and a processor coupled to the at least one emitter and the detector. The device further includes a non-transitory storage medium coupled to the processor and configured to store instruction to cause the device to perform the calibration method. Additionally, a calibration container includes a main body, upper lid, and a lower lid. The main body is configured to receive the device and an object having known optical properties.

18 Claims, 24 Drawing Sheets

(51) Int. Cl.

| | |
|---|---|
| *A61B 5/00* | (2006.01) |
| *A61B 5/02* | (2006.01) |
| *A61B 5/0205* | (2006.01) |
| *A61B 5/024* | (2006.01) |
| *A61B 5/0402* | (2006.01) |
| *A61B 5/1495* | (2006.01) |

(52) U.S. Cl.
CPC ...... *A61B 5/02007* (2013.01); *A61B 5/02438* (2013.01); *A61B 5/0402* (2013.01); *A61B 5/1455* (2013.01); *A61B 5/1495* (2013.01); *A61B 5/14532* (2013.01); *A61B 5/14535* (2013.01); *A61B 5/14546* (2013.01); *A61B 5/4875* (2013.01); *A61B 5/6828* (2013.01); *A61B 5/02416* (2013.01)

(56) References Cited

U.S. PATENT DOCUMENTS

| | | | |
|---|---|---|---|
| 2006/0211923 A1 | 9/2006 | Al-Ali et al. | |
| 2009/0177053 A1* | 7/2009 | Merchant | A61B 5/14552 600/323 |
| 2010/0179391 A1 | 7/2010 | Quintanar, II et al. | |
| 2013/0012787 A1 | 1/2013 | Horseman | |
| 2013/0016351 A1 | 1/2013 | Gono | |
| 2013/0204102 A1* | 8/2013 | Sen | A61B 5/14535 600/322 |
| 2014/0111807 A1 | 4/2014 | Yin et al. | |
| 2014/0275872 A1* | 9/2014 | Merritt | A61B 5/14551 600/322 |
| 2014/0275890 A1* | 9/2014 | Meehan | A61B 5/1495 600/324 |

\* cited by examiner

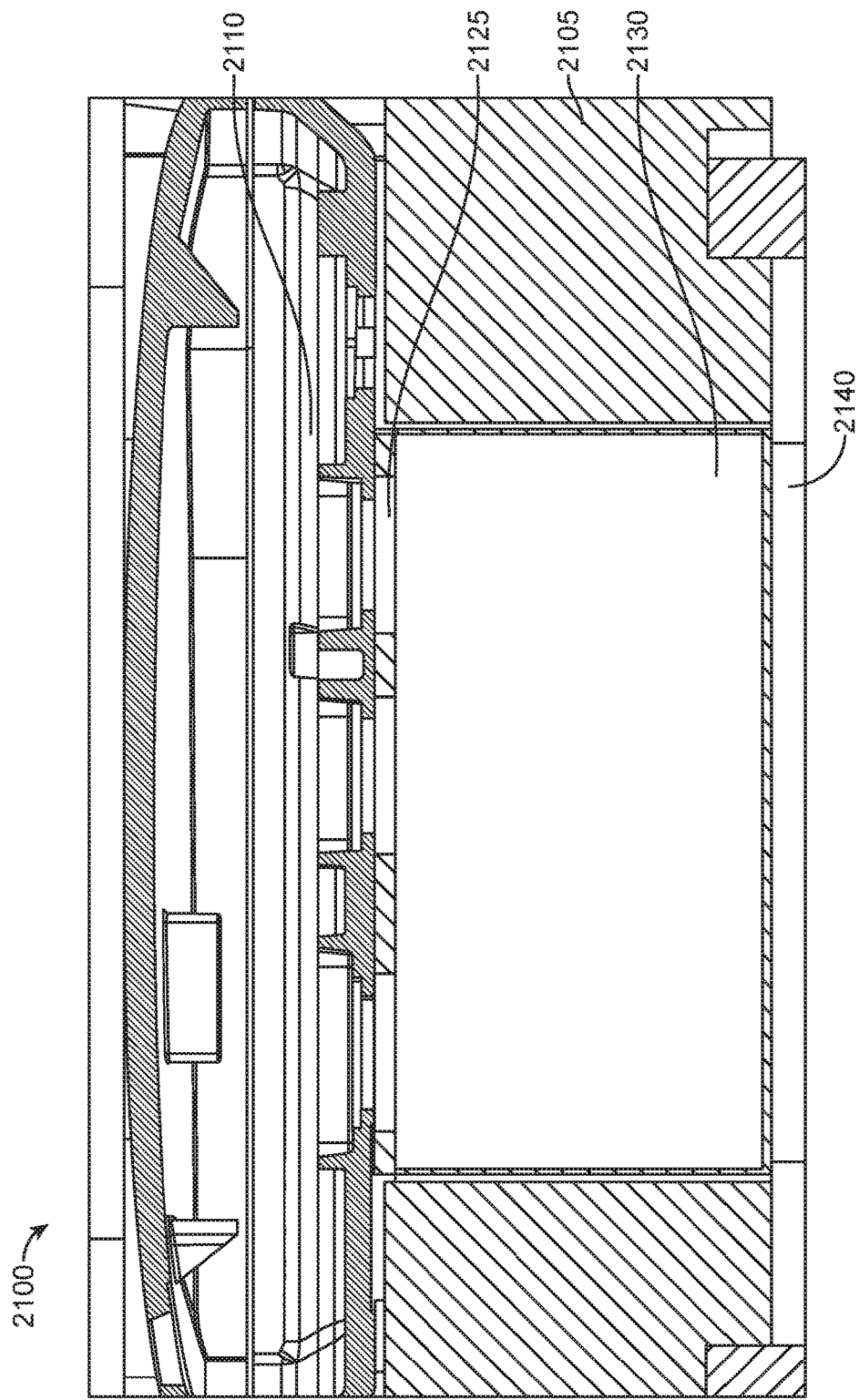

DEVICE AND METHOD FOR GENERATING CALIBRATION FACTORS FOR USE IN DETERMINING BIOLOGICAL INDICATOR LEVELS IN TISSUE

CROSS-REFERENCE TO RELATED APPLICATIONS

This application is U.S. National Stage Entry of PCT Application No. PCT/US2016/034403, filed May 26, 2016, which claims priority to U.S. Provisional Application No. 62/166,571 filed May 26, 2015, the entire contents of which are incorporated by reference.

FIELD

The present disclosure relates to calibrating a device based on an object having a known optical density.

BACKGROUND

Monitoring exertion via a heart rate monitor has long been a centerpiece of training for professional and performance athletes, as well as amateurs and retired players. Additional tests can be performed on the individual and involve taking measurements of the individual by a professional. For example, some methods involve drawing of blood from the individual. Specifically, in order to measure total hemoglobin (tHb), the individual has blood drawn and tests performed to determine the tHb level in the blood.

BRIEF DESCRIPTION OF THE DRAWINGS

In order to describe the manner in which the advantages and features of the disclosure can be obtained, reference is made to the appended drawings. The drawings presented provide only non-limiting examples of what is disclosed herein.

FIG. 21D is a cross-sectional view of a calibration container, according to an example of the present disclosure.

DETAILED DESCRIPTION

Figure 1:
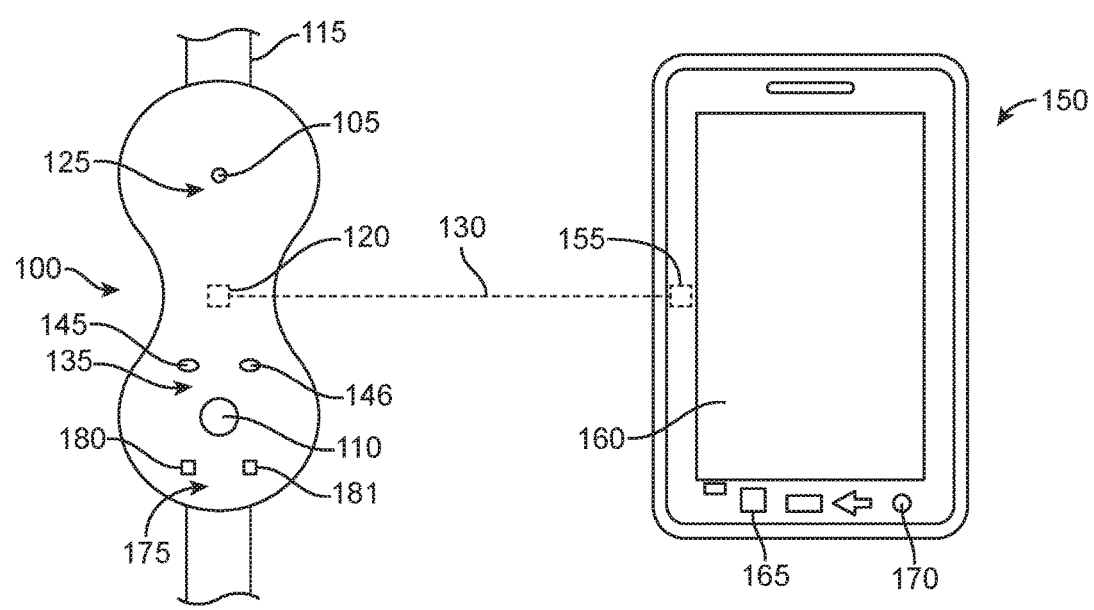
FIG. 1 is a schematic diagram of a non-invasive optical-electronic device, according to an example of the present disclosure.

Various examples of the disclosure are discussed in detail below. While specific implementations are discussed, it should be understood that this is done for illustration purposes only. A person skilled in the relevant art will recognize that other components and configurations can be used without parting from the spirit and scope of the disclosure.

It should be understood at the outset that although illustrative implementations of one or more examples are illustrated below, the disclosed devices, methods, and systems can be implemented using any number of techniques. The disclosure should in no way be limited to the illustrative implementations, drawings, and techniques illustrated herein, but can be modified within the scope of the appended claims along with their full scope of equivalents.

Unless otherwise specified, any use of any form of the terms "couple," or "attach," or any other term describing an interaction between elements is not meant to limit the interaction to direct interaction between the elements and also can include indirect interaction between the elements described. In the following discussion and in the claims, the terms "including" and "comprising" are used in an open-ended fashion, and thus should be interpreted to mean "including, but not limited to . . . ". As used herein, the term "spacing" refers to the distance between an emitter and a detector. The various characteristics described in more detail below, will be readily apparent to those skilled in the art with the aid of this disclosure upon reading the following detailed description, and by referring to the accompanying drawings.

The present disclosure generally relates to a non-invasive optical-electronic device configured to determine a level of optical density of different materials and, in particular, biological indicators within tissue or blood vessels. Examples of non-invasive optical-electronic devices configured to determine biological indicators are described in U.S. Pat. No. 8,996,088 entitled APPARATUS AND METHOD FOR IMPROVING TRAINING THRESHOLD, the entire contents of which are incorporated herein by reference. The optical-electronic device can be used by itself or in combination with other optical-electronic devices or biosensors. The optical-electronic device can be configured to determine physiological parameters of a user during exercise. It is to be understood, however, that the non-invasive optical-electronic device can also be used in other applications without departing from the principles of the present disclosure, including microcirculation analysis, newborn perfusion deficit, assessment of hemorrhage and shock, monitoring of fluid resuscitation, cognitive studies, cerebral oxygenation monitoring during cardiothoracic procedures, muscular oxygenation monitoring to diagnose acute and chronic compartment syndrome, and the monitoring of coronary artery disease (CAD) and other cardiovascular diseases.

The present disclosure generally relates to a device configured to measure physiological parameters of a user. In at least one example, the device can be a non-invasive optical electronic device. In one example, an optical-electronic device is configured to determine the level of optical density of a material, in particular biological indicators within tissues or blood vessels using Near Infrared Spectroscopy (NIRS). The device includes a processor which calculates a relative match between a spectral data set representative of received light and a predetermined spectral data set of one or more chromophores. The optical-electronic device can be configured to transmit an alert to an output device. The optical-electronic device can be further configured to communicate a level of a biological indicator to a user in real-time.

In a further example, an optical-electronic device is configured to determine the level of a biological indicator within tissues or blood vessels, which is further configured to alert a user to the existence of extraneous factors which interfere with the identification and/or determination of one or more biological indicators. The device can determine the existence of an extraneous factor by determining a modulus of a residual of the fit of a projection onto a matrix containing the spectra representative of a predetermined data set of one or more chromophores. The device can also determine the existence of an extraneous factor by determining the relative match of a spectral data set representative of received light and the null space for a matrix containing the spectra representative of a predetermined data set of one or more chromophores.

In a further example, an optical-electronic device is configured to determine the level of one or more biological indicators during exercise and other physical conditions.

In another example, a method is configured to determine the level of one or more biological indicators using an optical-electronic device configured to determine the level of a biological indicator within tissues or blood vessels using Near Infrared Spectroscopy (NIRS). The method includes calculating a relative match between a spectral data set representative of received light and a predetermined spectral data set of one or more chromophores. The method can further include transmitting an alert to an output device. The method can further include communicating a level of a biological indicator to a user in real-time.

In another example, a method is configured to determine the level of a biological indicator within tissue or vessels. The method includes emitting light into a tissue, detecting the light, and transmitting data representative of the received reflected light. The method can also include processing the data representative of the received reflected light with a processor having a non-transitory storage medium configured to store instructions to cause the processor to receive the data representative of the received reflected light. The method can also include comparing, via a processor, the data representative of the received reflected light to a predetermined spectral data set of one or more chromophores corresponding to a biological indicator. The method can also include calculating, via a processor, a relative match between the data representative of the received reflected light to the predetermined spectral data set. The method can also include estimating, via a processor, a level of a biological indicator based on the calculated relative match. The method can also include transmitting, via the processor, the level of a biological indicator to an output device. The method can also include transmitting, via a processor, an alert to an output device.

In another example, a calibration method includes converting optical data into a parameter corresponding to the attenuation properties of a biological tissue. The method includes generating a calibration factor to convert detected light into optical densities for a given light intensity, optical power, or optical irradiance, which can be based on a current, voltage, or using neutral density filters. The method can also include emitting light from at least two emitters into a tissue, where the at least two emitters are separated by a known distance. Additionally, the at least two emitters can have different known spacings from the detector. The method can include receiving detected light data from the tissue at a photodetector. The method can also include receiving current data from the tissue at a electrocardiography (EKG) sensor. The method can also include converting detected light data into optical densities for a given light intensity, or optical power or optical irradiance (hereinafter referred to as intensity) using the calibration factor. The method can include converting the optical densities into effective attenuation coefficients using optical densities determined from light data received from the two emitters separated by a known distance, and therefore have different known spacings from the detector. The method can also include converting the effective attenuation coefficients into absorption coefficients using a reduced scattering coefficient obtained for the tissue being monitored, where the absorption coefficient corresponds to the attenuation properties of the tissue.

In a further example, a method can be used to determine a level of a biological indicator in a tissue. The method can be based on the calibration optical data. The method includes generating a calibration factor to convert detected light into optical densities for a given intensity, emitting light from at least two emitters into a tissue, where the two emitters are separated by a known distance, and therefore have different known spacings from the detector. The method can also include converting detected light data into optical densities for a given intensity using the calibration factor. The method can include converting the optical densities into effective attenuation coefficients. The method can also include converting the effective attenuation coefficients into absorption coefficients using a reduced scattering coefficient obtained for the tissue being monitored, where the absorption coefficient corresponds to the attenuation properties of the tissue, and using the relative match of the absorption coefficient to predetermined spectral data to determine the level of a biological indicator in the tissue. The method can further include communicating a level of a biological indicator to a user in real-time.

According to at least one example of the present disclosure, a device is configured to generate a calibration factor for use in determining optical density. The device includes at least one emitter having at least one light source. In one example, the light source of the emitter can be a light emitting diode (LED) or any type of light source including lasers, laser diodes, vertical cavity surface emitting lasers (VCSEL) and light filtered from broadband sources, which include halogen lamps. In at least one example, all of the light sources can be an LED. An LED is an effective light source for the present disclosure since the LED has a dominate wavelength and the light intensity can be varied by the current. LEDs are also widely available and economical. Lasers (including laser diodes, edge emitting lasers, external cavity lasers, gas lasers, crystal lasers and VCSELs) have the benefit of emitting at a narrow band of wavelengths. The emitter is configured to emit light. The device further includes a detector configured to receive light and transmit data representative of the received light. The device also includes a processor coupled to the at least one emitter and the detector. The device further includes a non-transitory storage medium coupled to the processor and configured to store instructions to cause the device to emit light from the at least one light source of the at least one emitter at a predetermined intensity towards an object that has a known optical density, detect, at the detector, a portion of the emitted light corresponding to the predetermined intensity, calculate, at the processor, a corresponding calibration factor based on the detected portion of emitted light through the object, and store the corresponding calibration factor in the non-transitory storage medium.

In a further example, the device further includes a non-transitory storage medium having instructions to cause, repeatedly for each light source and each of a plurality of predetermined intensities, the device to emit light from one of the at least one light source of the at least one emitter at one of the plurality of predetermined intensities towards the object, detect, at the detector, a portion of the emitted light corresponding to the predetermined intensity, calculate, at the processor, a corresponding calibration factor based on the detected portion of emitted light through the object, and store the corresponding calibration factor in the non-transitory storage medium.

In a further example, the at least one emitter includes a plurality of emitters with each of the plurality of emitters having a plurality of light sources. In a further example, the device further includes a non-transitory storage medium having instructions to cause the device to emit light, towards the object, from one of the plurality of light sources of one of the emitters at one of a plurality of predetermined intensities, detect, at the detector, a portion of the emitted light corresponding to the one of a the plurality of predetermined intensities, calculate, at the processor, a corresponding calibration factor based on the detected portion of emitted light through the object, and store the corresponding calibration factor in the non-transitory storage medium.

In a further example, the device further includes at least two emitters each comprising at least one light source. In a further example, the device further includes a non-transitory storage medium having instructions causing the processor to repeat the following for each light source: emit light, towards the object, from one light source of one of the emitters at a predetermined intensity; detect, at the detector, a portion of the emitted light corresponding to the predetermined intensity; calculate, at the processor, a corresponding calibration factor based on the detected portion of emitted light through the object; and store the corresponding calibration factor in the non-transitory storage medium.

In a further example, the predetermined intensity comprises a plurality of intensities and each of the steps are performed for each of the plurality of intensities. In a further example, the at least two emitters are spaced at different distances from the detector. In a further example, the device further includes a non-transitory storage medium having instructions to cause the device to confirm that a calibration factor is stored for each light source at the plurality of intensities. In at least one example, the intensities can be based on a predetermined current. In a further example, the calculation of the corresponding calibration factor is derived using the formula: $C_{ijm}=10^{OD_{jm}}/D_{ijm}$, where is an index tracking a light intensity value, which in at least one example is a predetermined current value, j is an index tracking a light source, m is an index tracking a spacing between the light source and detector, OD is the optical density, and D is measured light data. In other examples as indicated above, the light intensity value can be any one of a current, voltage, or using neutral density filters.

In a further example, the non-transitory storage medium further includes instructions, upon receiving a measurement command, to: emit, iteratively, light from one of a plurality of light sources at one of a plurality of predetermined intensities towards the object of interest; detect, at a detector, a portion of the emitted light corresponding to a respective one the light sources and predetermined intensities; determine an optical density of the object of interest based on the calibration factors.

In a further example, the corresponding calibration factor is transmitted via a network interface component to a server. In a further example, the corresponding calibration factor is transmitted via a network interface component to an external electronic device. In a further example, the object is made of a material that is designed to mimic a biological tissue (that is, with reduced scattering and effective attenuation coefficients in the range of those of biological tissue within the range of wavelengths spanned by the light sources). In a further example, the at least one emitter comprises at least two emitters that are spaced apart from each other and from the detector. In a further example, one of the emitters is further away from the detector than the other. In a further example, each of the emitters are arranged along a ray extending from the detector. In a further example, each of the emitters are located on the same side of the detector. In a further example, each of the two emitters include a plurality of LEDs or light sources. In a further example, each of the two emitters includes four LEDs or light sources. In a further example, each of the plurality of LEDs or light sources within a given one of the least two emitters has a different peak wavelength of emission.

According to at least one example of the present disclosure, a method for calculating at least one calibration factor for an electronic device is configured to generate output data regarding a biological indicator. In at least one example, a set of calibration factors can be generated such that there is a calibration factor that corresponds to each combination of illuminator, spacing, and intensity combination. Additionally, as described below, the set of calibration factors can also consider the object from which the calibration factors are based such that there are different sets corresponding to the different objects. The method includes emitting light from each one of a plurality of light sources of at least one emitter at a first one of a plurality of predetermined intensity, detecting, at a detector, a portion of the emitted light corresponding to the first predetermined intensity, calculating, at the processor, a corresponding calibration factor based on the detected portion of emitted light, and storing the corresponding calibration factor in the non-transitory storage medium.

In a further example, the method further includes repeatedly, for the remaining ones of the plurality of predetermined intensities: emitting light from each one of the plurality of light sources of the at least one emitter; detecting, at a detector, a portion of the emitted light; calculating, at the processor, a corresponding calibration factor based on the detected portion of emitted light; and storing the corresponding calibration factor in the non-transitory storage medium.

In a further example, the predetermined intensity comprises a plurality of intensities and each of the steps are performed for each of the plurality of intensities. In a further example, the at least two emitters are spaced at different distances from the detector. In a further example, the method further includes confirming that a calibration factor is stored for each light source at the plurality of predetermined intensities. In at least one example, the plurality of predetermined intensities are based on a plurality of predetermined currents. In a further example, the calculation of the corresponding calibration factor is derived using the formula: $C_{ijm}=10^{OD_{jm}}/D_{ijm}$, where i is an index tracking a predetermined light intensity value, which can be a current value, j is an index tracking a light source, m is an index tracking a spacing between the light source and detector, OD is the optical density, and D is measured light data. In other examples as indicated above, the light intensity value can be any one of a current, voltage, or using neutral density filters.

In a further example, the method further includes emitting, iteratively, light from one of a plurality of light sources at one of a plurality of predetermined intensities towards the object of interest, detecting, at a detector, a portion of the emitted light corresponding to a respective one the light sources and predetermined intensities, and determining an optical density of the object of interest based on the calibration factors. In a further example, the method can further include transmitting the corresponding calibration factor via a network interface component to a server. In a further example, the method can include transmitting the corresponding calibration factor via a network interface component to a server. In a further example, the object is made of a material that is designed to mimic a biological tissue.

In a further example, the at least one emitter comprises at least two emitters that are spaced apart from each other and from the detector. In a further example, one of the emitters is further away from the detector than the other. In a further example, each of the emitters can be arranged along a ray extending from the detector. In a further example, each of the emitters can be located on the same side of the detector. In a further example, each of the two emitters can include a plurality of LEDs or light sources. In a further example, each of the two emitters includes four LEDs or light sources. In a further example, each of the plurality of LEDs or light sources within a given one of the least two emitters has a different peak wavelength of emission.

According to at least one example of the present disclosure, a system including an electronic device and a hardware server is configured to generate a calibration factor for use in determining optical density. The system includes at least one emitter having at least one light source, the emitter configured to emit light. The system can further include a detector configured to receive light and transmit data representative of the received light. The system can also include a processor coupled to the at least one emitter and the detector. The system can further include a non-transitory storage medium coupled to the processor and configured to store instructions to cause the device to emit light from the at least one light source of the at least one emitter at a predetermined intensity towards an object that has a known optical density, detect, at the detector, a portion of the emitted light corresponding to the predetermined intensity, calculate, at the processor, a corresponding calibration factor based on the detected portion of emitted light through the object, and store the corresponding calibration factor in the non-transitory storage medium.

In a further example, the at least one emitter, the detector, the processor, and the non-transitory storage medium are located within the electronic device. In a further example, the at least one emitter, the detector, and the processor are located within the electronic device and the non-transitory storage medium is located within the server.

According to at least one example of the present disclosure, a method for calculating a calibration factor for an electronic device is configured to generate output data regarding an optical density. The method includes placing, iteratively, the electronic device on one of a plurality of objects, each having a known optical density, emitting, iteratively, light from one of a plurality of light sources at one of a plurality of predetermined intensities, detecting, at a detector, a portion of the emitted light corresponding to a respective one of the plurality of objects, light sources, and predetermined intensities, calculating, at the processor, a corresponding calibration factor based on the detected portion of emitted light, storing the corresponding calibration factor in the non-transitory storage medium, and determining that the non-transitory medium has a corresponding calibration factor for each combination of the plurality of objects, light sources, and predetermined intensities, wherein the calibration factors are stored in a plurality of matrices, each of the plurality of matrices corresponding to one of the plurality of objects.

In a further example, the method further includes generating a matrix of best fit calibration factors based on a linear fit of the plurality of matrices. In a further example, the method further includes placing the electronic device on an object of interest, emitting, iteratively, light from one of a plurality of lights sources at one of a plurality of predetermined intensities, detecting, at a detector, a portion of the emitted light corresponding to a respective one of the plurality of objects, light sources, and predetermined intensities, and determining an optical density of the object of interest based on the matrix of best fit calibration factors.

According to at least one example of the present disclosure, a device can be configured to generate a calibration factor for use in determining optical density. The device includes a plurality of light sources, each configured to emit light. The device can further include a detector configured to receive light and transmit data representative of the received light. The device can further include a processor coupled to the plurality of light sources and the detector. The device can also include a non-transitory storage medium coupled to the processor and configured to store instructions to cause the device to iteratively emit light from one of the plurality of LED at one of a plurality of predetermined intensity towards one of a plurality of objects, each of the plurality of objects having a known optical density, detect, at the detector, a portion of the emitted light, calculate, at the processor, a corresponding calibration factor based on the detected portion of emitted light through the object, store the corresponding calibration factor in the non-transitory storage medium, and determine that the non-transitory medium has a corresponding calibration factor for each combination of the plurality of objects, light sources, and predetermined intensities.

According to at least one example of the present disclosure, a calibration container can include a main body forming a through opening configured to receive a test sample on one side and an electronic device on another side. The electronic device is configured to emit light from a plurality of emitters and receive light at a detector. The calibration container can further include an upper lid coupled to the main body and configured to securely enclose the one side. The calibration container can also include an object having known optical properties. In other examples, the object can be obtained separately from the calibration container. The calibration container can further include a lower lid coupled to the main body and configured to securely enclose the another side. The calibration container can also include a first gasket configured to be mounted between the main body and the upper lid and a second gasket configured to be mounted between the main body and the lower lid.

In a further example, the calibration container can further include a support plate configured to hold the electronic device in close proximity to the object. In a further example, the support plate forms at least three through holes corresponding to locations of the plurality of emitters and the detector. In a further example, the support plate is coupled to the main body via a plurality of threaded connections.

In a further example, the calibration container can further include a lower elastic material that is coupled to lower lid and configured to press the object against the support plate. In a further example, the main body forms a first gasket groove, which is configured to receive a portion of the first gasket. In a further example, the main body forms a second gasket groove, which is configured to receive a portion of the second gasket.

In a further example, the lower lid is coupled to the main body via a plurality of threaded connections, thereby holding the object within the main body. In a further example, the main body forms a first and second support ledge configured to support the electronic device on a first side and a second side. In a further example, the calibration container can further include an upper elastic material coupled to the upper lid and configured to hold the electronic device in place against the first support ledge and the second support ledge. In a further example, the calibration container further includes a hinge configured to couple the upper lid to the main body. In a further example, the calibration container further includes a latch configured to releasably secure the upper lid to the main body. In a further example, the main body has a portion configured to receive the object.

In another example, a method is presented that determines a user-specific measure of a biological indicator in a tissue using a predetermined set of user-specific parameters. The method includes generating a set of user-specific parameters based on that user's biological indicator data collected during an assessment using an optical-electronic device configured to capture optical data of a tissue. The method can also include storing the set of user-specific parameters on a server. The method can include measuring a biological indicator in the tissue of the user during a physical activity using an optical-electronic device configured to capture optical data of a tissue. The method can also include calculating a user-specific measure of the biological indicator using the set of user-specific parameters stored on the server. The method can further include transmitting an alert to an output device, wherein the alert is configured to notify the user of a user-specific measure of a biological indicator. The method can further include communicating a level of a biological indicator to a user in real-time.

In a further example, a method is described for determining a user-specific measure of Total Oxygenation Index (TOI) in a tissue using predetermined user-specific lactate threshold (LT) assessment data. The method includes generating user-specific TOI data while performing a LT assessment using an optical-electronic device configured to capture optical data of a tissue. The method further includes calculating user-specific TOI adjustment parameters. The method can also include storing the LT assessment based user-specific TOI adjustment parameters on a server. The method can include measuring TOI in the tissue of the user during a physical activity using the optical-electronic device. The method can also include calculating a user-specific measure of TOI using the user specific TOI adjustment parameters stored on the server. The method can further include transmitting an alert to an output device, wherein the alert is configured to notify the user of a user-specific measure of TOI. The method can further include communicating a user-specific measure of TOI to a user in real-time.

According to at least one example of the present disclosure, a device is configured to determine a biological indicator. The device can include at least two emitters having at least one light emitting element, the at least two emitters configured to emit light. The device further includes a detector configured to receive light and transmit data representative of the received light. The device also includes a processor coupled to the emitter and the detector and a non-transitory storage medium coupled to the processor. The non-transitory storage medium can be configured to store instructions to cause the device to emit a first light from one of the at least two emitters at a first predetermined intensity, detect at least a portion of the of first emitted light at the detector, obtain a first calibration factor, from the non-transitory storage medium, corresponding to the first predetermined intensity, generate a first optical density corresponding to the first calibration factor, emit a second light from another one of the at least two emitters at the first predetermined intensity, detect at least a portion of the second emitted light at the detector, obtain a second calibration factor, from the non-transitory storage medium corresponding to the first predetermined intensity, generate a second optical density corresponding to the second calibration factor, convert the first and second optical density to an effective attenuation coefficient based on the separation of the one emitter and the another emitter, and generate a biological indicator from the effective attenuation coefficient.

In a further example, the device further includes a non-transitory storage medium that also includes instructions causing the processor to calculate a relative match between the detected light and a predetermined spectral data set of one or more chromophores corresponding to the biological indicator, and estimate a level of the biological indicator based on the calculated relative match. In a further example, the relative match is calculated between the detected light and the predetermined spectral data set representative of the one or more chromophores using one or more of inner products, vector projections, direction cosines, and a pseudo-inverse projection method. In a further example, an effective attenuation coefficient, $\mu_{eff}$, is calculated according to the equation $\mu_{eff}=0.192 \Delta OD-0.098$, where $\Delta OD=OD_{far}-OD_{near}$, where $OD_{far}$ is the optical density corresponding to emitter spaced farther from the detector and the $OD_{near}$ is the optical density corresponding to the emitter spaced nearer the detector. The optical density can be calculated for each emitter according to $OD_{jm}=\log_{10}(C_{ijm} \times D_{ijm})$, where $C_{ijm}$ is the calibration factor and $D_{ijm}$ is the detected light at light intensity i, wavelength j, and distance m. In a further example in which the predetermined spectral data set is an absorption coefficient, the detected light is converted from an effective attenuation coefficient into the absorption coefficient by combining it with a known reduced scattering coefficient. In other examples as indicated above, the light intensity value can be any one of a current, voltage, or using neutral density filters.

In a further example, a modulus of a residual of a fit of a projection onto a matrix containing a spectra representative of a predetermined data set of one or more chromophores is determined. In a further example, the relative match of a spectral data set representative of received light and a null space for a matrix containing the spectra representative of a predetermined data set of one or more chromophores is determined. In a further example, the one or more chromophores includes one or more of hemoglobin, myoglobin, cytochrome c, water, lipids, melanins, glucose or metabolites. In a further example, hemoglobin includes at least one of oxyhemoglobin, deoxyhemoglobin, and total hemoglobin. In a further example, the total hemoglobin and the water is further utilized to determine perfusion characteristics of one or more of hemoglobin concentration, pulsatile rhythm, blood volume, vascular tone, muscular tone, and angiogenesis. In a further example, myoglobin comprises at least one of oxymyoglobin, deoxymyoglobin, and total myoglobin. In a further example, metabolites include at least one of lactate and lactic acid. In a further example, the one or more chromophores includes water and the water is further utilized to measure a hydration level.

In a further example, the device further includes a non-transitory storage medium further configured to store instructions to cause the processor to calculate a relative ratio of the one or more chromophores. In a further example, the non-transitory storage medium is further configured to store instructions to cause the processor to calculate a relative addition of the one or more chromophores. In a further example, the non-transitory storage medium is further configured to store instructions to cause the processor to extract data associated with the one or more chromophores from data representative of the detected light. In a further example, the at least two emitters are configured to emit at least three wavelengths of light or at least three ranges of wavelengths. In a further example, the biological indicator comprises at least one of a relative percentage, a saturation level, an absolute concentration, a rate of change, an index relative to training threshold, and a threshold.

According to at least one example of the present disclosure, a method is configured to determine a biological indicator. The method includes emitting a first light from one of at least two emitters at a first predetermined intensity, detecting at least a portion of the first emitted light at a detector, obtaining a first calibration factor, from the non-transitory storage medium, corresponding to the predetermined intensity, generating a first optical density corresponding to the first calibration factor, emitting a second light from another one of the at least two emitters at the first predetermined intensity, detecting at least a portion of the second emitted light at the detector, obtaining a second calibration factor, from the non-transitory storage medium, corresponding to the predetermined intensity, generating a second optical density corresponding to the second calibration factor, converting the first and second optical density to an effective attenuation based on the separation of the one emitter and the another emitter, and generating a biological indicator from the effective attenuation.

FIG. 1 illustrates a non-invasive optical-electronic device 100, according to an example of this disclosure. The device 100 can be attached to a portion, such as a muscle mass, of a user via a strap 115. The device 100 can be used with an optional output device 150, such as a smartphone (as shown), a smart watch, computer, mobile phone, tablet, an electronic processing and displaying unit, cloud storage, or a remote data repository via a cellular network or wireless Internet connection.

The device 100 includes a sensor 125 that is configured to determine the level of a biological indicator within tissue or blood vessels using NIRS. The sensor 125 includes an optical emitter 105 and an optical detector 110. In general, the sensor 125 uses two or more low-power lasers, LEDs or quasi-monochromatic light sources and low-noise photodetecting electronics to determine the optical absorption of chromophores, such as water, hemoglobin in its multiple forms, including oxyhemoglobin ($HbO_2$), deoxyhemoglobin (HHb), oxymyoglobin, deoxymyoglobin, cytochrome c, lipids, melanins, lactate, glucose, myoglobin (including myoglobin at least one of oxymyoglobin, deoxymyoglobin, and total myoglobin) or metabolites. The metabolites can include at least one of lactate and lactic acid. Cytochrome c can be used, for example, to track muscle adaptation to training. In another example, the sensor 125 can use a broad-spectrum optical source and a detector sensitive to the spectral components of light, such as a spectrometer, or a charge-coupled device (CCD) or other linear photodetector coupled with near-infrared optical filters.

The optical-electronic device 100 can be configured to include a second sensor 135 configured to measure photoplethysmography (PPT) of the user. The second sensor 135 includes an optical emitter 145 and an optical detector 146. The device 100 also includes a third sensor 175 configured to measure electrocardiography (EKG) and derived systolic time intervals (STI) of the user. The third sensor 175 includes a first electrode 180 and a second electrode 181. The sensors 125, 135, 175 in the device 100 can measure NIRS parameters, electrocardiography, photoplethysmography, and derived systolic time intervals (STI) of the user. The optical-electronic device 100 also includes a processor that is configured to analyze data generated by the sensors 125, 135, 175 to determine a cardiac response to exercise and the supply, arteriovenous difference, utilization of oxygen by the muscle tissue and hydration of the muscular tissue.

In at least one example, the processor is configured to determine biological indicators, including, but not limited to a relative percentage, a saturation level, an absolute concentration, a rate of change, an index relative to a training threshold, and a threshold. In other cases, the processor is configured to determine perfusion characteristics such as pulsatile rhythm, blood volume, vascular tone, muscle tone, and angiogenesis from total hemoglobin and water measurements.

The device 100 can include a power supply, such as a battery, to supply power to the sensors 125, 135, 175 and other components in the device 100. In one example, the sensor 125 has a skin contact area of 3.5"×2". In other examples, the sensor 125 can be sized to fit on the forearm of a user. In still other examples, the sensor 125 can be sized to fit on the wrist of the user.

Figure 2A:
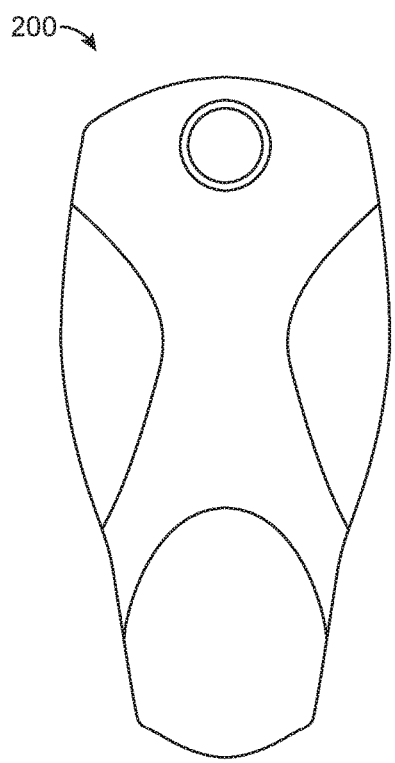
FIG. 2A is a schematic diagram of the front of a non-invasive optical-electronic device, according to an example of the present disclosure.
Figure 2B:
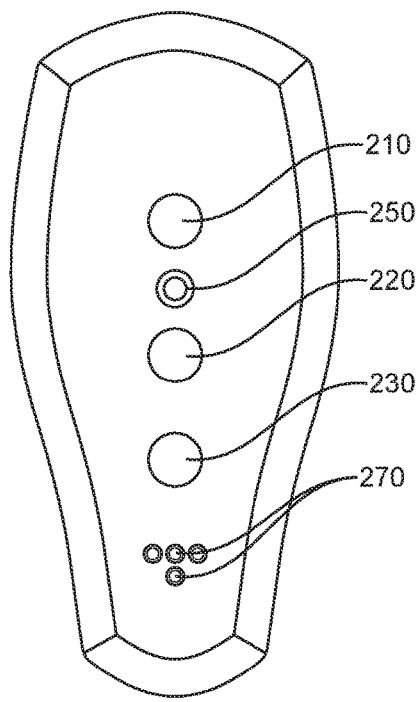
FIG. 2B is a schematic diagram of the back of a non-invasive optical-electronic device, according to an example of the present disclosure.

FIG. 2 illustrates a non-invasive optical-electronic device 200, according to an alternative example of this disclosure. The device 200 is configured to be worn on a limb of a user, such as on the calf muscle of a user's leg or the bicep of a user's arm. In at least one example, the device 200 can be optimized for a given limb, thereby increasing accuracy of the device. In other examples, the device 200 can be optimized based on the size, gender, or age of the user. In still other examples, a variety of the above optimizations can be implemented for a given device. FIG. 2A illustrates the front of the optical-electronic device. FIG. 2B illustrates the back of the optical-electronic device, including emitters 220, 230, 250 and photodetector 210. The device 200 also includes data and charging contacts 270. In at least one example, the data and charging contacts 270 can be used to electrically detect if the sensor is making contact with the skin of a user. The presence of multiple emitters 220, 230, 250 on the optical-electronic device allows for spatially-resolved data gathering in real-time. The optical-electronic device 200 can be configured to determine the optical absorption of chromophores, such as water, hemoglobin in its multiple forms, including oxyhemoglobin ($HbO_2$), deoxyhemoglobin (HHb), oxymyoglobin, deoxymyoglobin, cytochrome c, lipids, melanins, lactate, glucose, or metabolites.

Figure 2C:
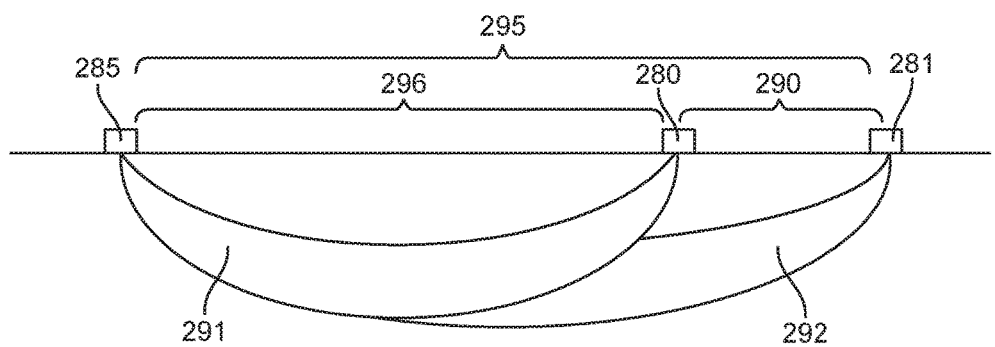
FIG. 2C is a schematic diagram of a spatially-resolved NIRS sensor that is included on a non-invasive optical-electronic device, according to an example of the present disclosure.

FIG. 2C illustrates a spatially-resolved NIRS sensor that can be included on the non-invasive optical-electronic device 200, according to an example of the disclosure. As shown in FIG. 2C, the spatially-resolved NIRS sensor includes light emitters 280 and 281 which emit light that is scattered and partially absorbed by the tissue. Each emitter 280, 281 can be configured to emit a single wavelength of light or a single range of wavelengths. In at least one example, each emitter 280, 281 can be configured to emit at least three wavelengths of light or at least three ranges of wavelengths. Each emitter 280, 281 can include one or more LEDs or light sources. Each emitter 280, 281 can include a low-powered laser, LED, or a quasi-monochromatic light source as a light source, or any combination thereof. Each emitter 280, 281 can also include a light filter.

A fraction of the light emitted by emitters 280 and 281 is detected by photodetector 285, as illustrated by the parabolic or "banana shaped" light arcs 291 and 292. Emitters 280, 281, are separated by a known distance 290, and therefore have different known spacings 295, 296 from the detector 285, and produce a signal that is later detected at photodetector 285. The detected signal is used to estimate the effective attenuation and absorption coefficients of the underlying tissue as described later in FIG. 6, for example at blocks 640 and 650. In at least one example, the known distance 290 between emitters 280, 281 is 12 millimeters. In at least one example, the 12 millimeter known distance between emitters 280 and 281 corresponds to a known spacing 295 of emitter 281 from detector 285 of 27 millimeters and a known spacing 296 of emitter 280 from detector 285 of 15 millimeters. In other examples, the known distance can be selected based on a variety of factors, which can include the wavelength of the light, the tissue involved, or the age of the user. While FIG. 2C depicts emitters 280, 281 arranged in a row and longitudinally spaced such that known distance 290 corresponds to a difference in the spacing between emitters 280, 281 and photodetector 285, the emitters can be spaced in any configuration so long as at least two of the emitters are spaced at different distances from photodetector 285.

The optical-electronic device 200 disclosed herein can have different numbers of emitters and photodetectors without departing from the principles of the present disclosure. Further, the emitters and photodetectors can be interchanged without departing from the principles of the present disclosure. Additionally, the wavelengths produced by the light sources can be the same for each emitter or can be different.

In at least one example, the device 200 is used for the monitoring of physiological parameters of a user during a physical activity. Use of the device 200 can be relevant in endurance type sports, such as running, cycling, multisport competition, rowing, but can also be used in other physical activities. The device 200 can be configured to wirelessly measure real-time muscle parameters during physical exercise. The device 200 can be secured to a selected muscle group of the user, such as the leg muscles of the vastus lateralis or gastrocnemius, which are primary muscle groups of running and cycling.

Figure 3:
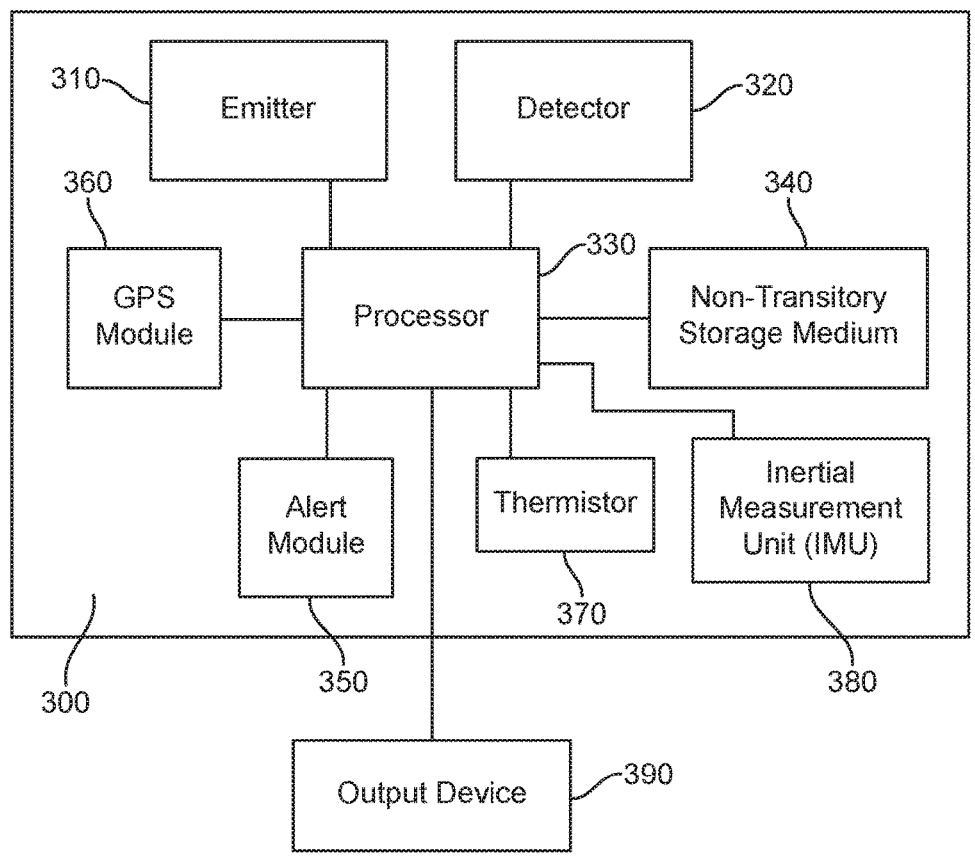
FIG. 3 illustrates the components of an optical-electronic device, according to an example of the present disclosure.

FIG. 3 illustrates the components of an optical-electronic device 300 according to an example of this disclosure. As shown in FIG. 3, the optical-electronic device includes an emitter 310 and detector 320, which are coupled to a processor 330. The processor 330 is coupled to a non-transitory storage medium 340. The device 300 is coupled to an output device 390.

The emitter 310 delivers light to the tissue and the detector 320 collects the optically attenuated signal that is back-scattered from the tissue. In at least one example, the emitter 310 can be configured to emit at least three separate wavelengths of light. In another example, the emitter 310 can be configured to emit at least three separate bands or ranges of wavelengths. In at least one example, the emitter 310 can include one or more light emitting diodes (LEDs) or light sources. The emitter 310 can also include a light filter. The emitter 310 can include a low-powered laser, LED, or a quasi-monochromatic light source, or any combination thereof, as a light source. The emitter can emit light ranging from infrared to ultraviolet light. As indicated above, the present disclosure uses NIRS as a primary example and the other types of light can be implemented in other examples and the description as it relates to NIRS does not limit the present disclosure in any way to prevent the use of the other wavelengths of light.

The data generated by the detector 320 can be processed by the processor 330, such as a computer processor, according to instructions stored in the non-transitory storage medium 340 coupled to the processor. The processed data can be communicated to the output device 390 for storage or display to a user. The displayed processed data can be manipulated by the user using control buttons or touch screen controls on the output device 390.

The optical-electronic device 300 can include an alert module 350 configured to generate an alert. The processor 330 can send the alert to the output device 390 or the alert module 350 can send the alert directly to the output device 390. In at least one example, the optical-electronic device 300 can be configured so that the processor 330 is configured to send an alert to the output device 390 without the device including an alert module 350.

The alert can provide notice to a user, via a speaker or display on the output device 390, of a change in biological indicator conditions or other parameter being monitored by the device 300, or the alert can be used to provide an updated biological indicator level to a user. In at least one example, the alert can be manifested as an auditory signal, a visual signal, a vibratory signal, or combinations thereof. In at least one example, an alert can be sent by the processor 330 when a predetermined biological indicator event occurs during a physical activity.

In at least one example, the optical-electronic device 300 can include a Global Positioning System (GPS) module 360 configured to determine geographic position and tagging the biological indicator data with location-specific information. The optical-electronic device 300 can also include a thermistor 370 and an inertial measurement unit (IMU) 380. The inertial measurement unit (IMU) 380 can be used to measure, for example, gait performance of a runner or pedal kinematics of a cyclist, as well as physiological parameters of a user during a physical activity. The thermistor 370 and inertial measurement unit (IMU) 380 can also serve as independent sensors configured to independently measure parameters of physiological threshold. The thermistor 370 and inertial measurement unit (IMU) 380 can also be used in further algorithms to process or filter the optical signal.

Figure 4:
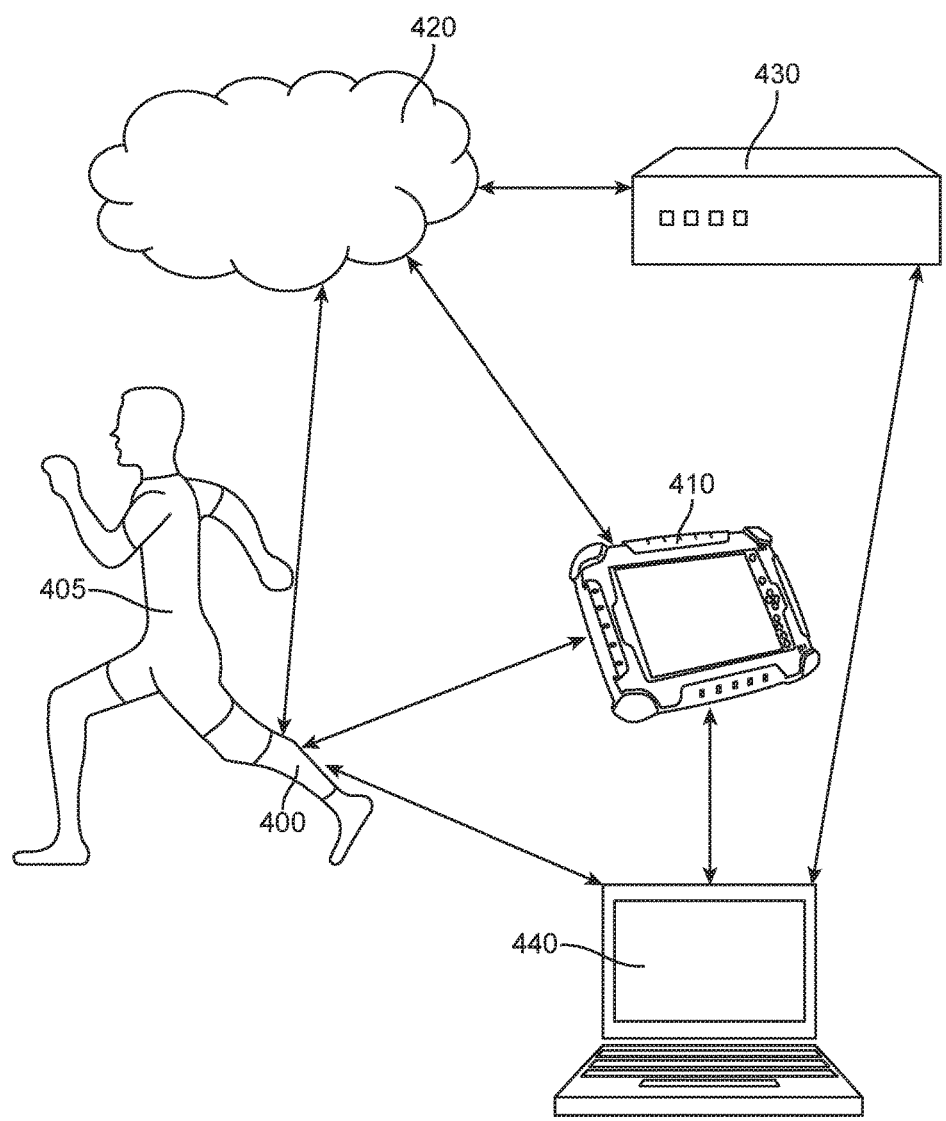
FIG. 4 illustrates an environment within which the non-invasive optical-electronic device can be implemented, according to an example of the present disclosure.

FIG. 4 illustrates an environment within which the non-invasive optical-electronic device 400 can be implemented, according to an example of this disclosure. As shown in FIG. 4, the optical-electronic device 400 is worn by a user to determine biological indicator levels during a physical activity. The optical-electronic device 400 is depicted as being worn on the calf of a user 405, however, the optical-electronic device 400 can be worn on any portion of the user suitable for monitoring biological indicator levels. The device 400 can be used with an output device 410, such as a smartphone (as shown), a smart watch, computer, mobile phone, tablet, an electronic processing and displaying unit, cloud storage, or a remote data repository via a cellular network or wireless Internet connection.

As shown in FIG. 4, the optical-electronic device 400 communicates with a output device 410 so that data collected by the optical-electronic device 400 is displayed or transferred to the output device 410 for communication of real-time biological indicator data to the user 405. In at least one example, an alert can be communicated from the device 400 to the output device 410 so that the user 405 can be notified of a biological indicator event. Communication between the device 400 and the output device 410 can be via a wireless technology, such as BLUETOOTH®, infrared technology, or radio technology, or can be through a wire. Transfer of data between the optical-electronic device 400 and the output device 410 can also be via removable storage media, such as a secure digital (SD) card. In at least one example, a display unit can be substituted for the output device 410.

The optical-electronic device 400 also communicates with a personal computing device 440 or other device configured to store and/or display user-specific biological indicator data. The personal computing device 440 can include a desktop computer, laptop computer, tablet, smartphone, smart watch, or other similar device. Communication between the device 400 and the personal computing device 440 can be via a wireless technology, such as BLUETOOTH®, infrared technology, or radio technology. In other examples, the communication between the device 400 and the personal computing device 440 can be through a wire or other physical connection. Transfer of data between the optical-electronic device 400 and the personal computing device 440 can also be via removable storage media, such as an SD card.

The output device 410 can communicate with a server 430 via a network 420, allowing transfer of user-specific biological indicator data to the server 430. The output device 410 can also communicate user-specific biological indicator data to cloud-based computer services or cloud-based data clusters via the network 420. The output device 410 can also synchronize user-specific biological indicator data with a personal computing device 440 or other device configured to store or display user-specific biological indicator data. The output device 410 can also synchronize user-specific biological indicator data with a personal computing device 440 or other device configured to both store and display user-specific biological indicator data. Alternatively, the personal computing device 440 can receive data from a server 430 or cloud-based computing service via the network 420.

The personal computing device 440 can communicate with a server 430 via a network 420, allowing the transfer of user-specific biological indicator data to the server 430. The personal computing device 440 can also communicate user-specific biological indicator data to cloud-based computer services or cloud-based data clusters via the network 420. The personal computing device 440 can also synchronize user-specific biological indicator data with the output device 410 or other device configured to store and/or display user-specific biological indicator data.

The optical-electronic device 400 can also directly communicate data via the network 420 to a server 430 or cloud-based computing and data storage service. In at least one example, the device 400 can include a GPS module configured to communicate with GPS satellites (not shown) to obtain geographic position information.

The optical-electronic device 400 can be used by itself or in combination with other optical-electronic devices or biosensors. For example, the optical-electronic device 400 can be used in combination with heart rate (HR) biosensor devices, foot pod biosensor devices, and/or power meter biosensor devices. The optical-electronic device 400 can also be used in combination with ANT+™ wireless technology and devices that use ANT+™ wireless technology. The optical-electronic device 400 can be used to aggregate data collected by other biosensors including data collected by devices that use ANT+™ technologies. Aggregation of the biosensor data can be via a wireless technology, such as BLUETOOTH®, infrared technology, or radio technology, or can be through a wire.

The biosensor data aggregated by the optical-electronic device 400 can be communicated via a network 420 to a server 430 or to cloud-based computer services or cloud-based data clusters. The aggregated biosensor data can also be communicated from the optical-electronic device 400 to the output device 410 or personal computing device 440.

In at least one example, the optical-electronic device 400 can employ machine learning algorithms by comparing data collected in real-time with data for the same user previously stored on a server 430, output device 410, or in a cloud-based storage service. The machine learning algorithm can also be performed on or by any one of the output device 410, cloud-based computer service, server 430, or personal computing device 440, or any combination thereof.

According to this disclosure, determination of the level of a biological indicator within tissue or blood vessels is achieved by calculating a relative match, or indices, between the spectral data received at the detector with a predetermined spectral data set of one or more chromophores corresponding to the biological indicator. In at least one example, the predetermined spectral data set corresponds to the signal spectra of specific analytes that can be readily obtained from the literature. See for example, Analyt. Biochem. Vol 227, pp. 54-68 (1995). The relative match calculation is performed by calculating a projection of the spectral data set captured from a user in the direction of the predetermined spectral data set in order to calculate an index that reflects the proximity of the match. The spectral projection method can be used to calculate a relative percentage level of a biological indicator or, with proper calibration, can be used to calculate the absolute concentration of a biological indicator.

The spectral projection method of determining the level of a biological indicator can be implemented mathematically using the inner product method which will be explained, by way of example, using the Total Oxygenation Index (TOI) as the biological indicator of interest. TOI is the ratio of the oxygenated hemoglobin ($HbO_2$) to total hemoglobin (tHb), where total hemoglobin (tHb) is equal to the combined concentrations of the oxygenated hemoglobin ($HbO_2$) and the chromophore deoxygenated hemoglobin (HHb):

$$TOI=[HbO_2]/[tHb] \text{ or } TOI \% =100*([HbO_2]/[tHb]),$$
$$\text{where } [tHb]=[HbO_2]+[HHb].$$

TOI, as used herein, includes the more specific parameter, $SmO_2$, which is the muscle oxygen saturation. $SmO_2$ can also be the tissue oxygen saturation determined from optical measurements of muscle tissue. Both oxygenated hemoglobin ($HbO_2$) and deoxygenated hemoglobin (HHb) are chromophores for which a spectral data set can be predetermined. The notation O(D) can be used to denote the predetermined spectral data for oxyhemoglobin (deoxyhemoglobin) at the same wavelengths for which the spectral data set for a user was measured at the detector, and U can be used to denote the measured data set, including an effective attenuation ($\mu_{eff}$) or an effective absorption coefficient ($\mu_a$). The inner product method of calculating the spectral projection can be calculated according to different mathematical methods, including, but not limited to, a direction cosine method, vector projection method, and a pseudo-inverse projection method:

Direction Cosine Method:

$$TOI = \frac{\langle U, O \rangle}{\left\langle U, O + D\sqrt{\frac{\langle O, O \rangle}{\langle D, D \rangle}} \right\rangle},$$

Vector Projection Method:

$$TOI = \frac{\langle U, O \rangle}{\left\langle U, O + D\sqrt{\frac{\langle O, O \rangle}{\langle D, D \rangle}} \right\rangle},$$

Pseudo-Inverse Projection Method:

$$TOI = \frac{\left\langle U, O - \frac{\langle O, D \rangle}{\langle D, D \rangle} D \right\rangle}{\left\langle U, O\left[1 - \frac{\langle O, D \rangle}{\langle D, D \rangle}\right] + D\left[\frac{\langle O, O \rangle}{\langle D, D \rangle} - \frac{\langle O, D \rangle}{\langle D, D \rangle}\right] \right\rangle}.$$

All of these methods can be rewritten as $$TOI = \frac{\langle U, O - aD \rangle}{\langle U, O(1-a) + D(b-a) \rangle}$$

where a and b are scalars defined as i) $a = 0, b = \sqrt{\frac{\langle O, O \rangle}{\langle D, D \rangle}}$;

ii) $a = 0, b = \frac{\langle O, O \rangle}{\langle D, D \rangle}$; and iii) $a = \frac{\langle O, D \rangle}{\langle D, D \rangle}$ and $b = \frac{\langle O, O \rangle}{\langle D, D \rangle}$ for the cosine, vector projection and pseudo-inverse methods, respectively.

Figure 5A:
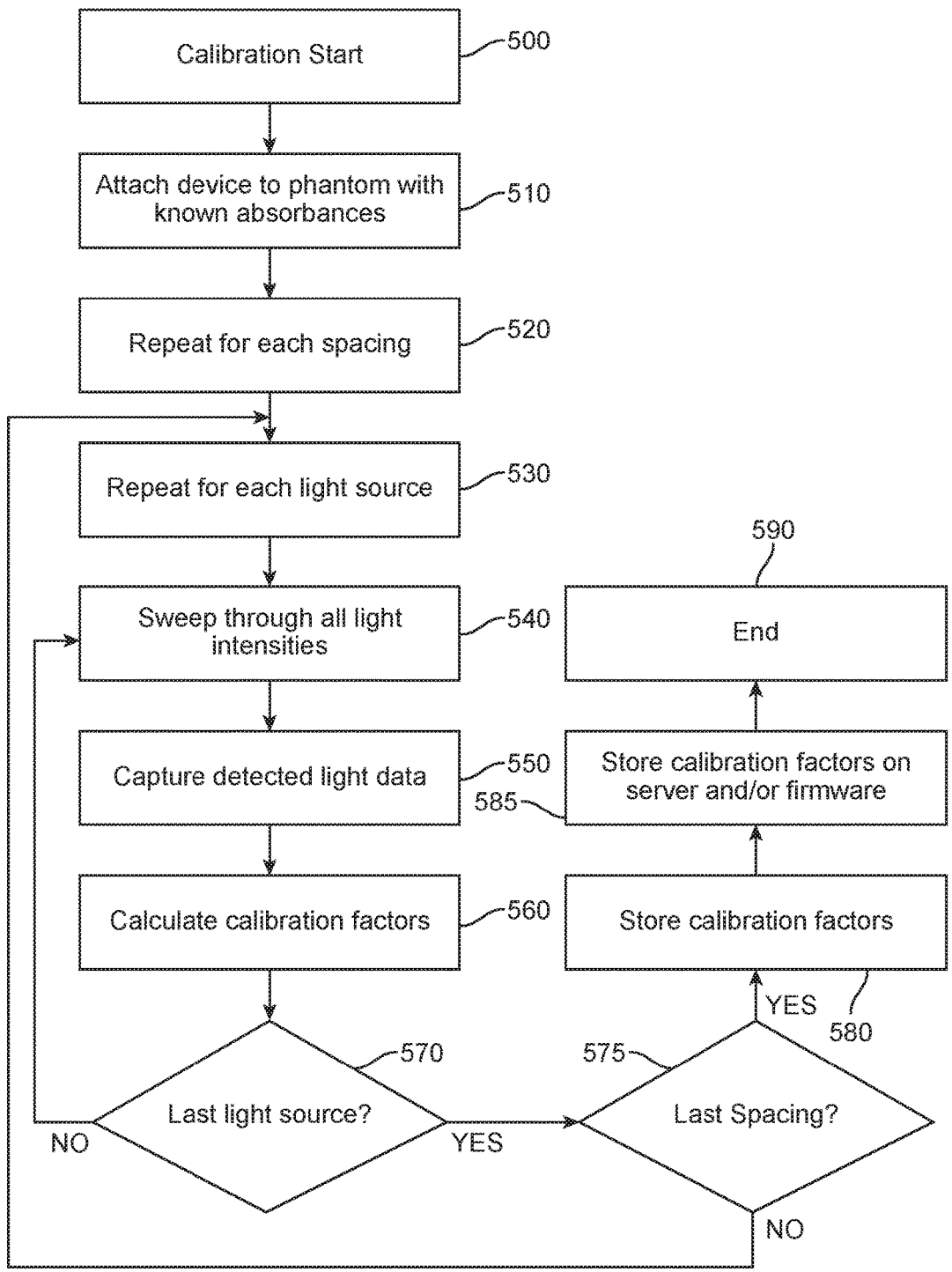
FIG. 5A is a flowchart describing a method of generating calibration factors used to convert detected light data into optical densities, according to an example of the present disclosure.
Figure 5B:
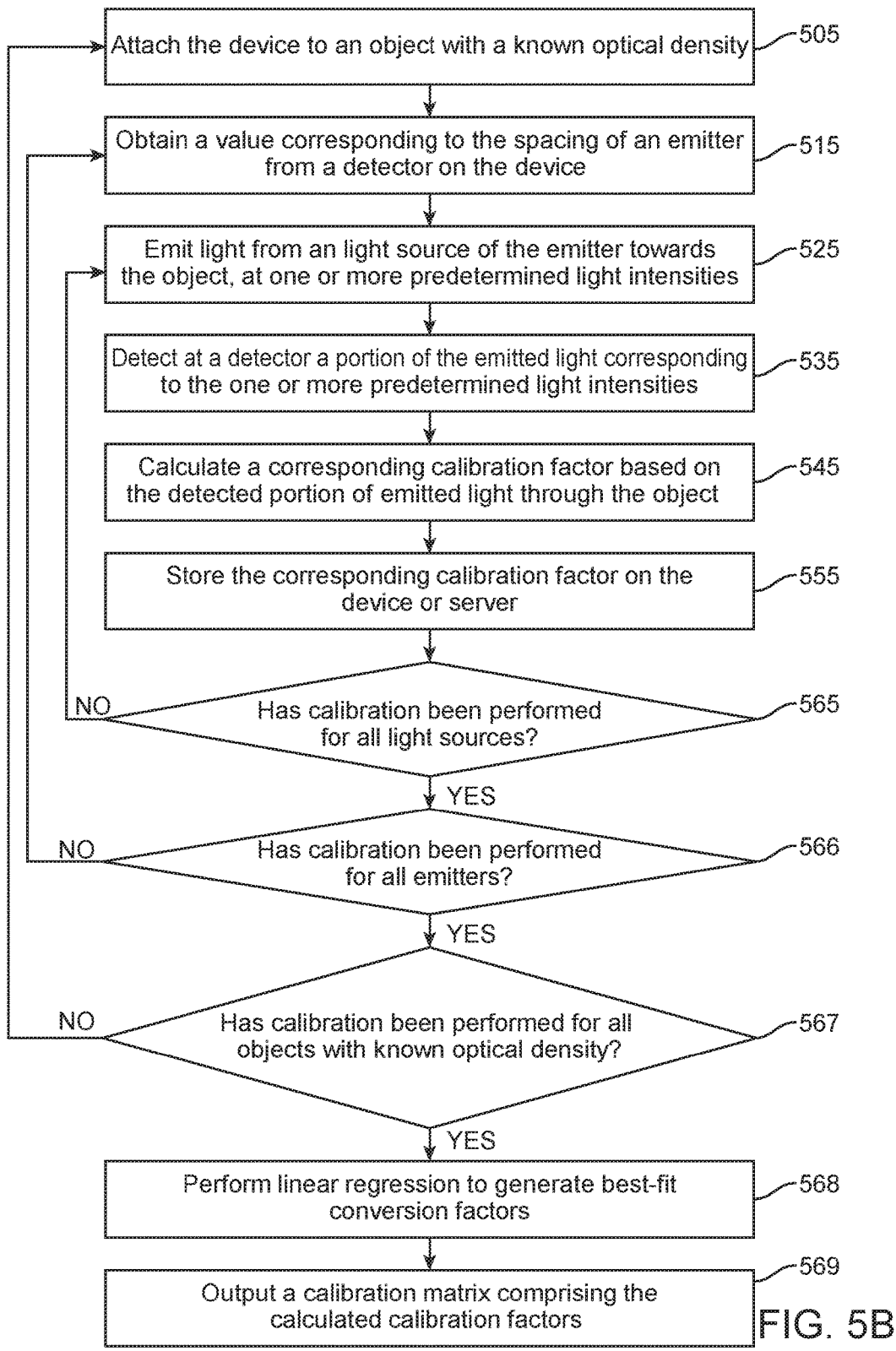
FIG. 5B is a flowchart describing a method of generating calibration factors, using one or more objects with known optical densities, for converting detected light data into optical densities, according to an example of the present disclosure.

Prior to calculating indices, calibration coefficients can be generated which allow the indices calculation to be corrected for the absorption properties of the tissue. FIGS. 5A and 5B are flowcharts describing methods used to generate the calibration coefficients that can be used, for example, by the projection indices algorithm.

Referring to FIG. 5A, a flowchart is presented in accordance with an example. The example method shown in FIG. 5A is provided by way of an example, as there are a variety of ways to carry out the method. Each block shown in FIG. 5A represents one or more processes, methods, or subroutines, carried out in the example method shown in FIG. 5A. Furthermore, the illustrated order of blocks is illustrative only and the order of the blocks can change according to the present disclosure. Additional blocks can be added or fewer blocks can be utilized, without departing from this disclosure.

The example calibration method can begin at block 500. At block 510, the optical-electronic device can be attached, located in close proximity, or otherwise situated adjacent to an object with known absorbances $OD_{jm}$. In at least one example, the object can be a phantom, which has been configured with special optical properties. In one example, the special optical properties can be that to resemble tissue. While phantom is used herein, other objects are considered within the scope of the present disclosure. This procedure is repeated for each spacing m at block 520 and for each light source or light source wavelength, j, at block 530. At block 540, all light intensities, i, are swept. At block 550, light data $D_{ijm}$ are captured. The calibration factors are calculated at block 560, using the formula: $C_{ijm}=10^{OD_{jm}}/D_{ijm}$. In other examples as indicated above, the light intensity can be any one of a current, voltage, or using neutral density filters.

Block 570 determines whether the calibrations algorithm has been repeated for each light source. If the calibration has not been performed for one or more light sources the blocks beginning with block 540 are repeated for the additional light source until all light sources have been calibrated. Block 575 determines whether the calibration has been performed for all separation distances between the emitters and a detector. If it is determined that calibration has not been performed for all distances between the emitters and a detector, the blocks beginning with block 530 are repeated until the last light source and last spacing has been calibrated, upon which the calibration factors are stored in block 580. Calibration factors $C_{ijm}$ are stored on a server and/or the firmware in block 585. The calibration algorithm is completed in block 590. The calibration factors stored according to the method described in FIG. 5A, can be used, for example, by the projection indices algorithm shown in FIG. 6.

The phantom used in the method described in FIG. 5A can be any suitable solid phantom, including, but not limited to optical-grade quality polymers that simulate a wide variety of tissues in the VIS-NIR. In at least some instances, the phantom can comprise a polymer, a scattering agent, and a light absorbing dye. In at least some instances, the polymer can be, but is not limited to, polyurethane or a polyurethane-based polymer. The scattering agent can be, but is not limited to titanium dioxide ($TiO_2$). The absorbing dye can be, but is not limited to, carbon black. In some instances, the phantom can comprise a polyurethane-based polymer further including a scattering agent and an absorbing dye. In at least some instances, the phantom can be a Biomimic™ Optical Phantom available from INO of Quebec, Canada (www.ino.ca).

The phantom can be manufactured to have predetermined light scattering and light absorption characteristics. For example, the phantom can be manufactured to have a predetermined absorption coefficient ($\mu_a$) at a reference wavelength and/or a predetermined scattering coefficient ($\mu_s'$) at a reference wavelength. For example, the predetermined light scattering and light absorption characteristics of the phantom can be engineered by changing the amount of scattering agent and absorbing dye in the polymer phantom. In at least some instances, the method described in FIG. 5A can further include selecting a phantom having a light absorption and light scattering characteristics that mimic the tissue for which the optical electronic device will determine a biological indicator.

Referring to FIG. 5B, a flowchart is presented in accordance with an example. The example method shown in FIG. 5B is provided by way of an example, as there are a variety of ways to carry out the method. Each block shown in FIG. 5B represents one or more processes, methods, or subroutines, carried out in the example method shown in FIG. 5B. Furthermore, the illustrated order of blocks is illustrative only and the order of the blocks can change according to the present disclosure. Additional blocks can be added or fewer blocks can be utilized, without departing from this disclosure.

FIG. 5B provides an example calibration method that can be used for calibrating an optical-electronic device having one or more emitters, each having one or more LEDs, spaced from a detector by different spacings. The example calibration method provided in FIG. 5B includes placing in proximity or otherwise adjacent the optical-electronic device to one or more objects having a known optical density. In one example, the optical-electronic device can be attached to one or more objects having a known optical density. While a single object having a known optical density is sufficient to perform the calibration, using multiple objects having a known optical density can, at least in some instances, provide an improved set of calibration factors. According to the method provided in FIG. 5B, each calibration using an object having a known optical density provides a separate set of calibration factors, thus allowing the determination of a best-fit set of calibration factors, that may be determined, for example, by calculating a linear regression. Thus, the method of FIG. 5B, in at least some instances, provides for minimization of error between the set of calibration factors and the true calibration factors.

The example calibration method can begin at block 505. At block 505, the optical-electronic device can be attached, located in close proximity, or otherwise situated adjacent to an object with a known optical density $OD_{jm}$. At block 515, a value corresponding to the spacing, m, of an emitter from a detector on the optical-electronic device is obtained. At block 525, light having wavelength, j, is emitted from a light source of an emitter, at one or more predetermined light intensity, i, towards the object having a known optical density. A portion of the emitted light corresponding to the one or more predetermined light intensities, $D_{ijm}$, is detected at a detector at block 535. In other examples as indicated above, the light intensity value can be any one of a current, voltage, or using neutral density filters.

At block 545, a corresponding calibration factor based on the detected portion of emitted light through the object is calculated using the formula: $C_{ijm}=10^{OD_{jm}}/D_{ijm}$. The corresponding calibration factor is stored on the device or on a server at block 555. Block 565 determines whether calibration blocks 525 to 555 have been performed for each light source of an emitter. If calibration blocks 525 to 555 have not been performed for one or more light sources of an emitter, the blocks beginning with block 525 are repeated for the additional light source until calibration has been performed for all light sources of an emitter.

Block 566 determines whether calibration blocks 515 to 555 have been performed for each emitter. If it is determined that calibration blocks 515 to 555 have not been performed for all emitters, the blocks beginning with block 515 are repeated until calibration has been performed for all emitters. Thus, the method provides for calibration of each emitter which each emitter potentially having a unique spacing distance between the emitter and the detector.

Block 567 determines whether calibration blocks 505 to 555 have been performed for each object having a known optical density. If it is determined that calibration blocks 505 to 555 have not been performed for each object having a known optical density, the blocks beginning with block 505 are repeated until calibration has been performed for all objects having a known optical density. As previously described, the method described in FIG. 5B may be performed using only a single object having a known optical density. However, the use of multiple objects, each having a different known optical density can allow, at least in some instances, for the optical-electronic device to be accurately used within a wider range of materials.

In instances in which multiple objects having different known optical densities are used, calibration blocks 505 to 567 produce S sets of calibration factors $C_{ijm}$, where S is the number of calibration objects employed. Then, once the last object having a known optical density is calibrated, a linear fit between the calibration factors $C_{ijm}$ and the optical densities $OD_{jm}$ is performed at block 568, resulting in the best fit calibration factors $C_{ijm}$. The best fit calibration factors can then be stored on the device or on a server or output as a calibration matrix at block 569. In instances in which only a single object having a known optical density is used, the calibration factors $C_{ijm}$ can be output to a calibration matrix, at block 569, comprising the calculated calibration factors, without performing block 568. The calibration factors $C_{ijm}$ stored according to the method described in FIG. 5B, can be used, for example, by the projection indices algorithm shown in FIG. 6.

The object having a known optical density used in the method described in FIG. 5B can be any suitable solid object having known optical properties, including, but not limited to optical-grade quality polymers that simulate a wide variety of tissues in the VIS-NIR. In at least some instances, the object having a known optical density can comprise a polymer, a scattering agent, and a light absorbing dye. In at least some instances, the object having a known optical density can be, but is not limited to, polyurethane or a polyurethane-based polymer. The scattering agent can be, but is not limited to titanium dioxide (TiO$_2$). The absorbing dye can be, but is not limited to, carbon black. In some instances, the objecting having a known optical density can comprise a polyurethane-based polymer further including a scattering agent and an absorbing dye. In at least some instances, the object having a known optical density can be a Biomimic™ Optical Phantom available from INO of Quebec, Canada (www.ino.ca).

In at least some instances, the method described in FIG. 5B can further include selecting an object having a known optical density that has optical characteristics that mimic the tissue for which the optical electronic device will determine a biological indicator. In other instances, the method described in FIG. 5B may be performed using multiple objects having known optical densities. In such instances, the method can further include selecting the objects having known optical densities to have optical properties that mimic the optical properties of the range of human tissues in the VIS-NIR spectra for which the optical electronic device will determine a biological indicator. For example, the object or objects having a known optical density can be manufactured to have predetermined light scattering and light absorption characteristics. More specifically, the objects or objects having a known optical density can be manufactured to have a predetermined absorption coefficient ($\mu_a$) at a reference wavelength and/or a predetermined scattering coefficient ($\mu_s'$) at a reference wavelength. For example, the predetermined light scattering and light absorption characteristics of an object having a known optical density can be engineered by changing the amount of scattering agent and absorbing dye in the polymer that comprises the object having a known optical density.

Figure 6:
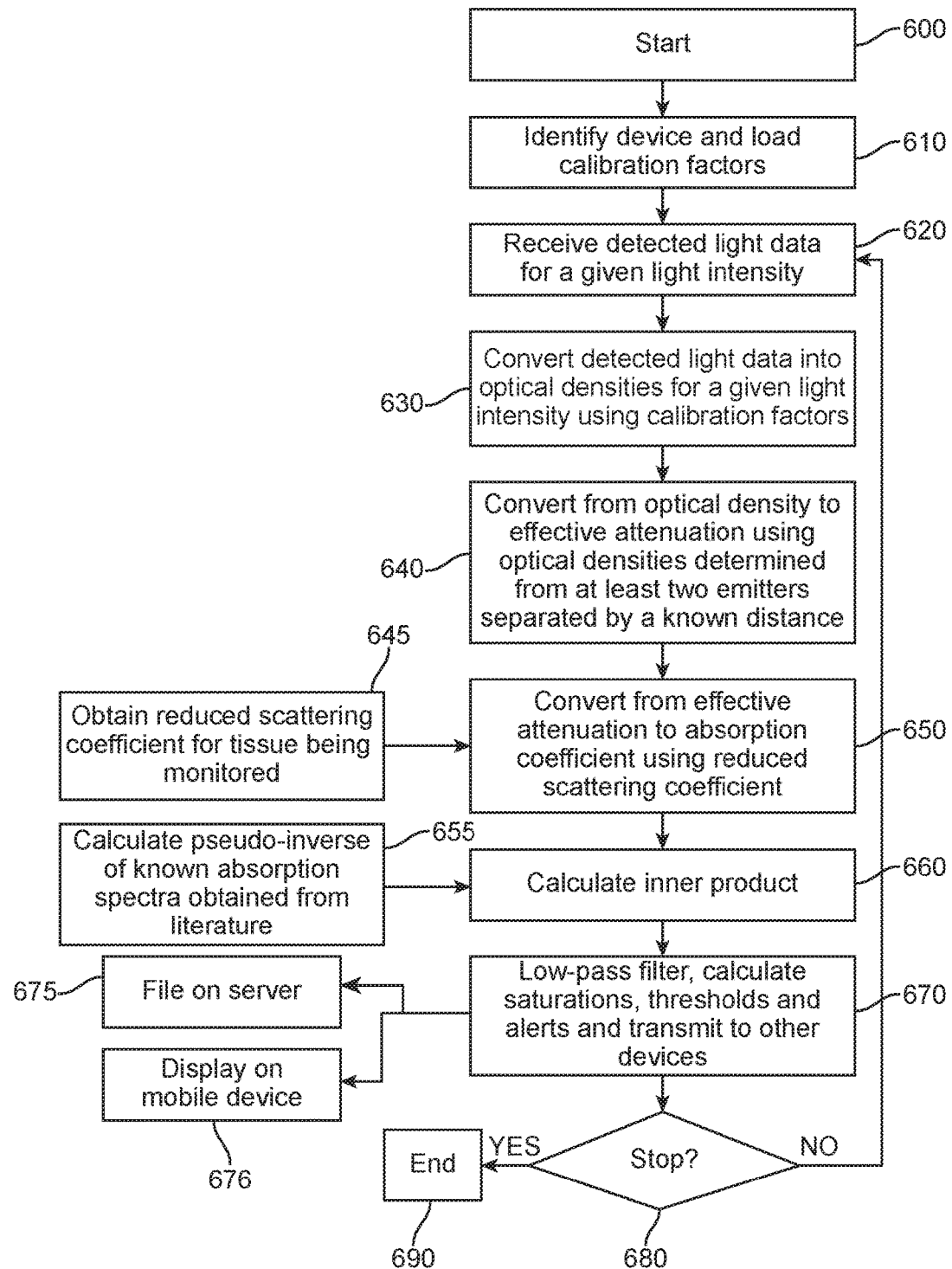
FIG. 6 is a flowchart describing a spectral projection algorithm used to calculate indices from spectral data, according to an example of the present disclosure.

Referring to FIG. 6, a flowchart is presented in accordance with an example. The example method shown in FIG. 6 is provided by way of an example, as there are a variety of ways to carry out the method. Each block shown in FIG. 6 represents one or more processes, methods, or subroutines, carried out in the example method shown in FIG. 6. Furthermore, the illustrated order of blocks is illustrative only and the order of the blocks can change according to the present disclosure. Additional blocks can be added or fewer blocks can be utilized, without departing from this disclosure.

FIG. 6 describes a spectral projection algorithm used to calculate indices from spectral data. The example algorithm can begin at block 600. At block 610, the optical-electronic device is identified and the calibration factors $C_{jm}$ are loaded onto the device. At block 620, the detected light data $D_{jm}$ is received by the device for a given light intensity i. The detected light data are converted into optical densities for a given light intensity i using the calibration factors $C_{jm}$, at block 630, using the equation: $OD_{jm}=\log_{10}(C_{ijm}\times D_{ijm})$. In other examples as indicated above, the light intensity value can be any one of a current, voltage, or using neutral density filters.

At block 640, the optical densities are converted to effective attenuations using optical densities determined from at least two emitters separated from the detector by a known distance. The slope of the optical density varies with respect to the effective attenuation according to the following expression:

$$\frac{dOD}{d\rho} = \mu_{\mathit{eff}}\log_{10}e + \frac{2}{\rho\ln 10},$$

in which $\rho$ denotes the distance between light source and detector. Accordingly, the effective attenuation can be determined from the slope of the preceding expression. Alternatively, in an example in which there are two different spacings, such as one emitter that is 15 millimeters from the detector and one emitter that is 27 millimeters from the detectors, resulting in a distance between spacings of 12 millimeters, we have $\mu_{\mathit{eff}}(j)=0.192(OD_{j2}-OD_{j1})-0.098$. At block 650, the effective attenuations are converted to absorption coefficients, according to the equation: $\mu_a(j)=0.5[\mathrm{sqrt}(\mu_{s'}(j)^2+4/3\mu_{\mathit{eff}}(j)^2)-\mu_{s'}(j)]$, where $\mu_{s'}(j)$ is the reduced scattering coefficient for tissue being monitored, taken from the literature in block 645. For example, from Applied Optics, Vol. 36, No. 1, pp. 386-396 (1997). The inner product is calculated at block 660, according to the equation: $P_k=\Sigma_j\mu_a$ (j)Finv$_{jk}$, where Finv$_{jk}$ is the pseudo-inverse of known absorption spectra at wavelengths j taken from the literature at block 655, and $\Sigma_j$ denotes summation over index j. At block 670, the inner product, P$_k$, obtained from the previous block is processed using a low-pass filter and displayed on a mobile device or display at block 676 and/or sent to a server for storage and transmission across a network at block 675. Additionally, saturations and thresholds are calculated at block 670 and displayed on a mobile device or display and/or sent to a server for storage and transmission across a network. Block 670 further generates an alarm, alert or notification based upon the calculated indices, saturations, and/or thresholds and displays the alarm, alert, or notification on a mobile device or display. At block 680, the spectral projection algorithm stops if the device is set to intermittent monitoring or in the case of constant monitoring by spectral analysis, the blocks beginning with block 620, can be repeated. In at least one example, the spectral projection algorithm described in FIG. 6 can be used to display biological indicator data to a user in real-time.

Figure 7:
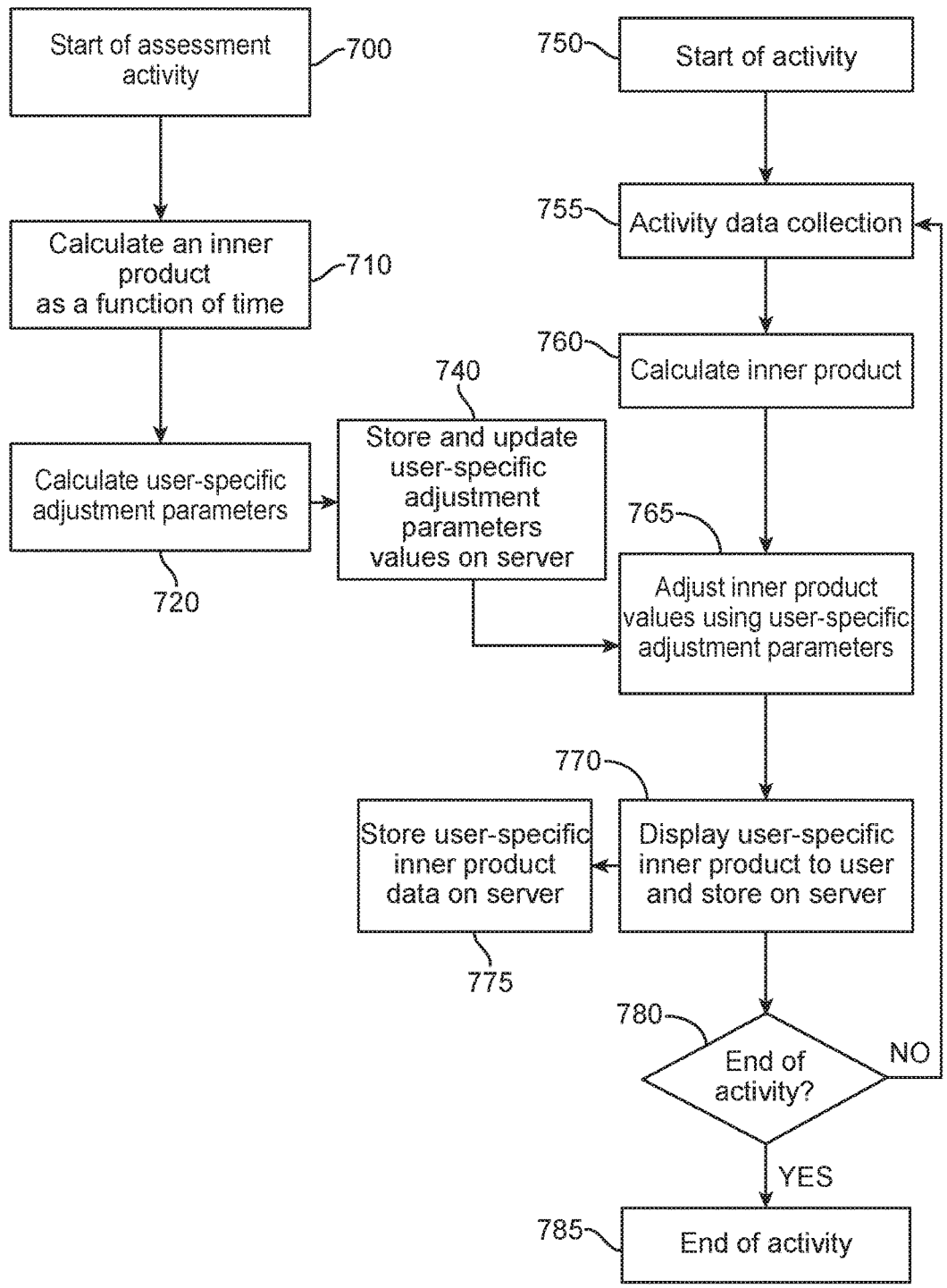
FIG. 7 is a flowchart describing an algorithm for user-specific adjustment of calculated indices, according to an example of the present disclosure.

Referring to FIG. 7, a flowchart is presented in accordance with an example. The example method shown in FIG. 7 is provided by way of an example, as there are a variety of ways to carry out the method. Each block shown in FIG. 7 represents one or more processes, methods, or subroutines, carried out in the example method shown in FIG. 7. Furthermore, the illustrated order of blocks is illustrative only and the order of the blocks can change according to the present disclosure. Additional blocks can be added or fewer blocks can be utilized, without departing from this disclosure.

FIG. 7 describes an algorithm for the generation of user-specific adjustment parameters and their use to provide personalized measurements of biological indicators during the activity of a user. In FIG. 7, the inner product as a function of time, P$_k$(t), obtained from the spectral projection algorithm, is calculated during an assessment activity, giving rise to customized user-specific adjustment parameters A$_k$(t). A$_k$(t) is calculated based on prior knowledge of how it should vary during a controlled exercise protocol, such as an assessment activity, thereby providing the algorithm with a user-specific set of customized parameters P$_k$(t)'.

The assessment activity can begin at block 700. An example of an assessment activity that can be performed according to this disclosure is a Lactate Threshold (LT) assessment. However, it should be understood by one skilled in the art that the present disclosure is equally well-suited for use with other assessment activities, controlled exercise protocols, and with any biological indicators configured to be measured using the optical-electronic device. At block 710, an inner product of the biological indicator of interest is calculated as a function of time. At block 720, user-specific adjustment parameters, such as Pk(t), and A$_k$(t) are calculated, thereby generating the user-specific set of parameters, A$_k$(t), which are stored in the server database and/or used to update the user-specific adjustment parameters on the server at block 740. The A$_k$(t) values are then used later when the user wants to measure P$_k$(t)', a more user specific version of P$_k$(t), during a physical activity.

The physical activity can be begun by the user at block 750. At block 755, activity data is collected. P$_k$(t) is calculated at block 760. At block 765, the P$_k$(t) values calculated at block 760, are adjusted using the user-specific set of parameters stored at block 740 (P$_k$(t)'=f[P$_k$(t), A$_k$(t)]). At block 770, the P$_k$(t)' data is displayed to the user and stored on the server at block 775. This algorithm, providing customized adjustment parameter monitoring to a user during a physical activity, continues until the user physical activity ends at block 785. The algorithm described in FIG. 7 can be repeated iteratively so as to routinely or constantly update the user-specific adjustment parameters on the server in order to display user-specific biological indicator levels using the latest or most up-to-date user-specific adjustment parameters. Additionally, learning algorithms can be used which compare data collected in real-time with previously collected data for the same user stored on a server.

Figure 8:
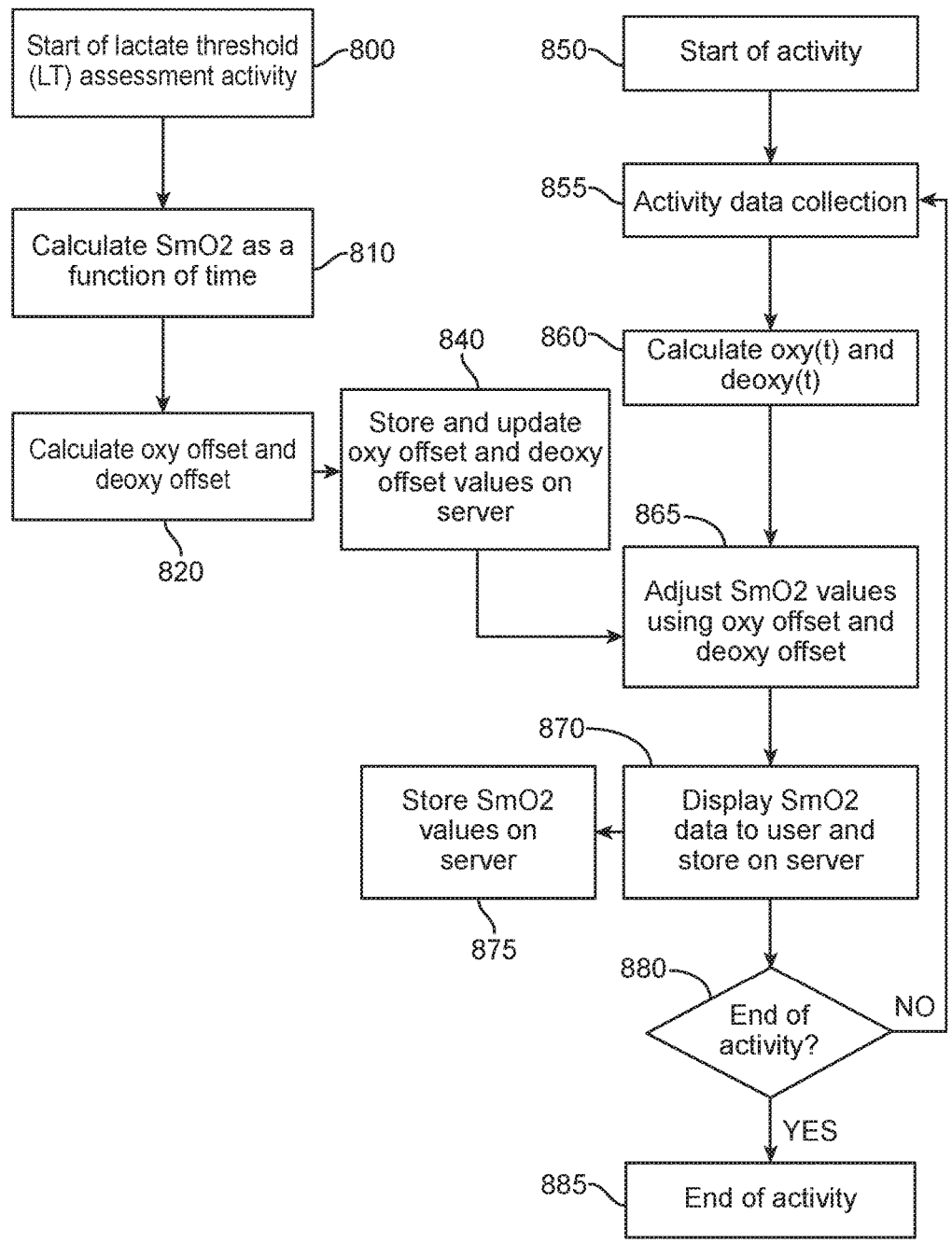
FIG. 8 is a flowchart describing an adaptive algorithm for user-specific adjustment of $SmO_2$ calculation during a user activity, according to an example of the present disclosure.

Referring to FIG. 8, a flowchart is presented in accordance with an example. The example method shown in FIG. 8 is provided by way of an example, as there are a variety of ways to carry out the method. Each block shown in FIG. 8 represents one or more processes, methods, or subroutines, carried out in the example method shown in FIG. 8. Furthermore, the illustrated order of blocks is illustrative only and the order of the blocks can change according to the present disclosure. Additional blocks can be added or fewer blocks can be utilized, without departing from this disclosure.

FIG. 8 describes an algorithm for adaptive SmO$_2$ calculation during a user activity, which can include any physical activity, for example jogging, biking, running, swimming, or exercising. This SmO$_2$ algorithm is a special case of the algorithm for customized parameter monitoring described in FIG. 7. SmO$_2$ is muscle oxygen saturation or tissue oxygen saturation determined from optical measurements of muscle tissue. SmO$_2$ is equal to the ratio of the oxyhemoglobin level divided by the total hemoglobin level, where the total hemoglobin level equals the oxyhemoglobin level plus the deoxyhemoglobin level. The algorithm described in FIG. 8 uses data collected during a lactate threshold (LT) assessment activity to increase the accuracy of SmO$_2$ results, thereby providing users with customized monitoring of SmO$_2$ values during a physical activity. While the algorithm described in FIG. 8 relies on a fixed offset of the oxyhemoglobin concentration, Oxy(t), and a fixed offset of the deoxyhemoglobin concentration, Deoxy(t), data calculated using, for example, indices from the spectral projection algorithm disclosed in FIG. 6, it should be understood by one skilled in the art that the present disclosure is equally well-suited for use with any other algorithm known to those skilled in the art, including but not limited to the multi-variate Beer-Lambert method.

The LT assessment activity can begin at block 800. At block 810, SmO$_2$ is calculated as a function of time. SmO$_2$ is calculated according to the equation: SmO$_2$=Oxy(t)/[Oxy(t)+Deoxy(t)]. At block 820, oxy offsets (A) and deoxy offsets (B) are calculated. At block 840, the A and B values are stored in a server database, or used to update the user-specific A and B values stored on the server. The A and B values are then used to increase the user specificity of SmO$_2$ determinations made during a physical activity.

The physical activity can be begun by the user at block 850. At block 855, activity data is collected. Oxy(t) and Deoxy(t) are calculated at block 860. At block 865, SmO$_2$ values are adjusted using the A and B data stored at block 840 (SmO$_2$=[Oxy(t)+A]/[Oxy(t)+A+Deoxy(t)+B]). At block 870, the SmO$_2$ data is displayed to the user and stored on the server at block 875. This algorithm, providing more specific SmO2 monitoring for a user during a physical activity, continues until the user physical activity ends at block 885.

The algorithm described in FIG. 8 can be repeated iteratively so as to routinely or constantly update the user-specific adjustment parameters on the server in order to display user-specific biological indicator levels using the latest or most up-to-date user-specific adjustment parameters. Additionally, learning algorithms can be used which compare data collected in real-time with previously collected data for the same user stored on a server.

Figure 9:
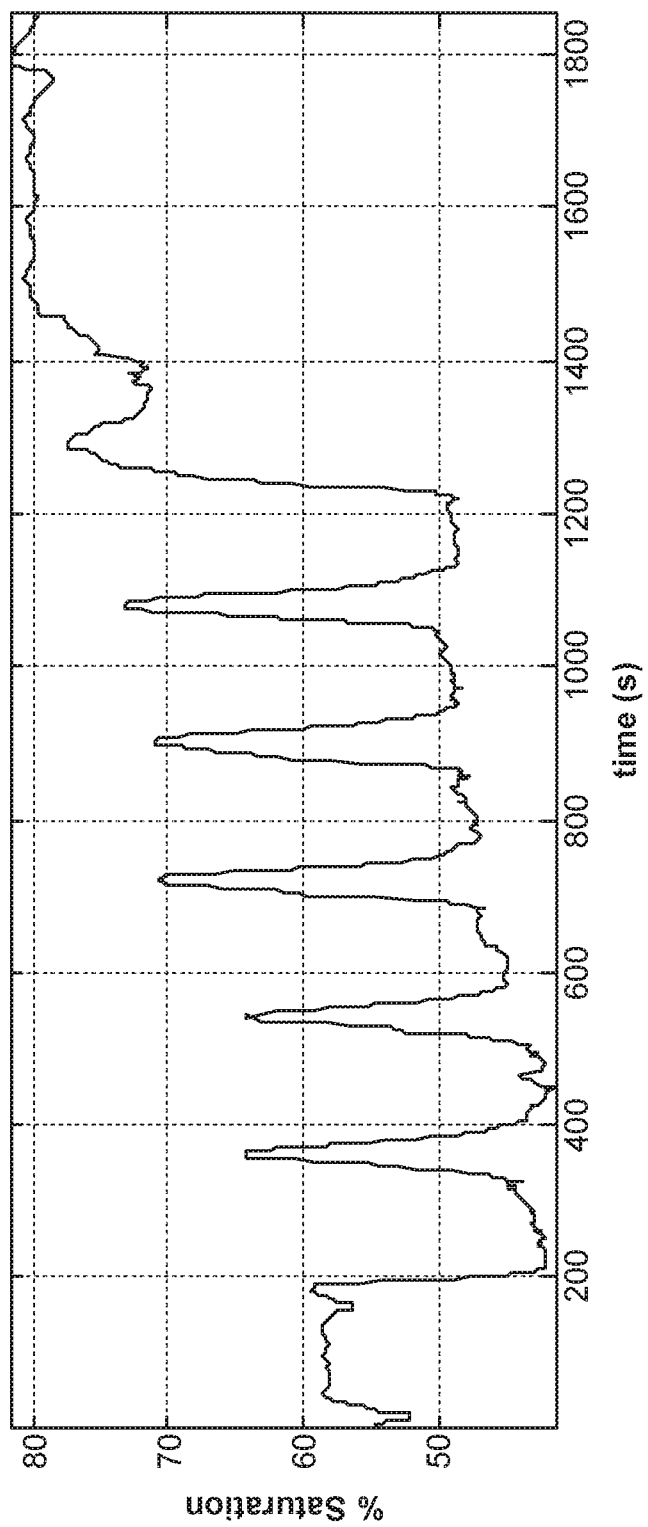
FIG. 9 is a plot illustrating Percentage (%) of Saturation $SmO_2$ versus time (s) for a user, calculated according to an example of the present disclosure.

FIG. 9 illustrates Percentage (%) of Saturation $SmO_2$ versus time (s), calculated according to the present disclosure, for a user running on a treadmill at a pace that increases every 180 s, with 30-second rest periods in between. As shown in FIG. 9, sharp peaks of oxygenation occur during the resting periods, demonstrating that the algorithm correctly tracks the expected increase in oxygenation that takes place during the resting periods.

Figures 10, 11:
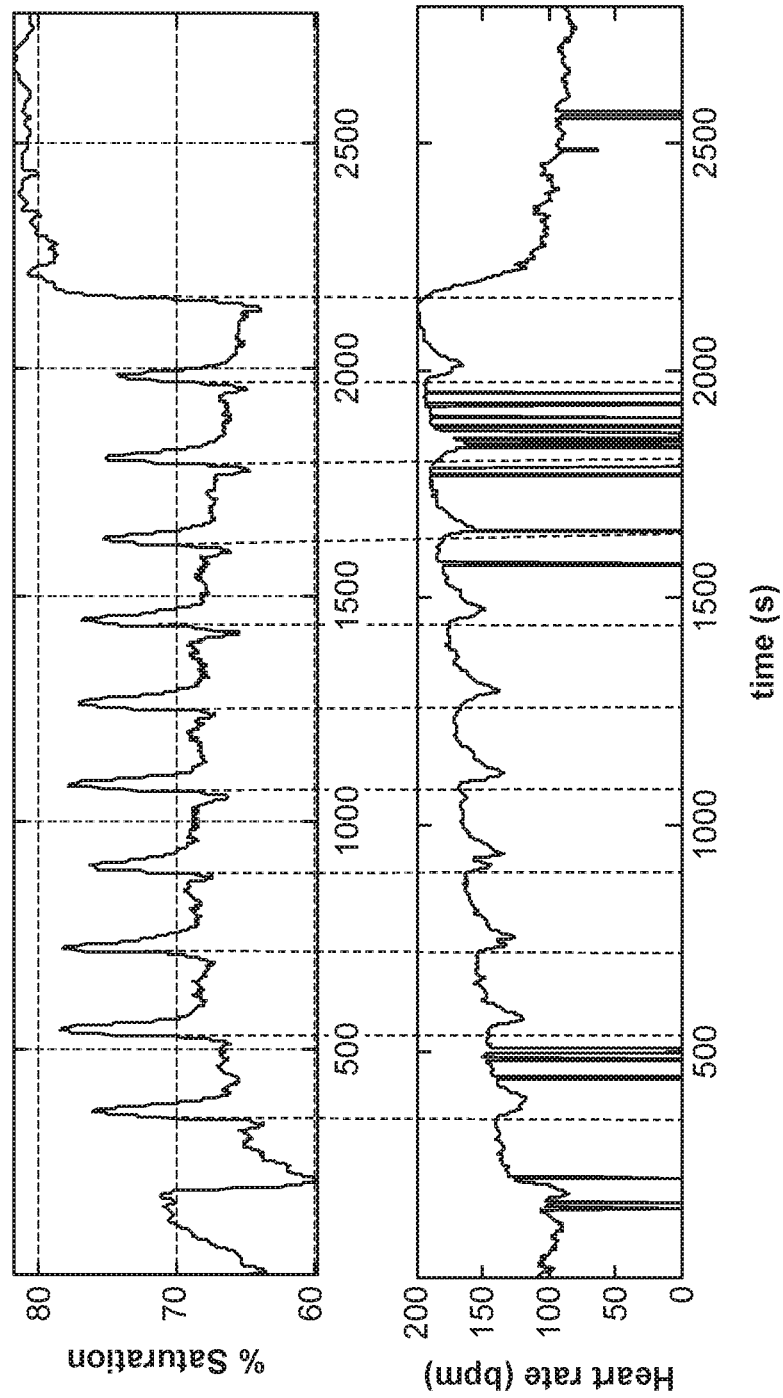
FIG. 10 is a plot illustrating Percentage (%) of Saturation $SmO_2$ versus time (s) for a user using the same test protocol used to collect the data shown in FIG. 9, but with an increased number of stages, according to an example of the present disclosure.
FIG. 11 is a plot of heart rate data corresponding to the plot of Percentage of Saturation of $SmO_2$ in FIG. 10, according to an example of the present disclosure.

FIG. 10 illustrates Percentage (%) of Saturation $SmO_2$ versus time (s) for a user using the same test protocol used to collect the data shown in FIG. 9 but with an increased number of stages (eleven stages instead of six stages). As shown in FIG. 10, the baseline signal drops after 1200 seconds, indicating that the user's maximum Percentage (%) Saturation during exertion was achieved at that point.

FIG. 11 is a plot of heart rate data corresponding to the plot of Percentage of Saturation of $SmO_2$ in FIG. 10, according to an example of the present disclosure. As shown in FIG. 11, the high oxygenation peaks are closely followed by drops in heart rate, as is expected to occur during the resting periods.

Figure 12:
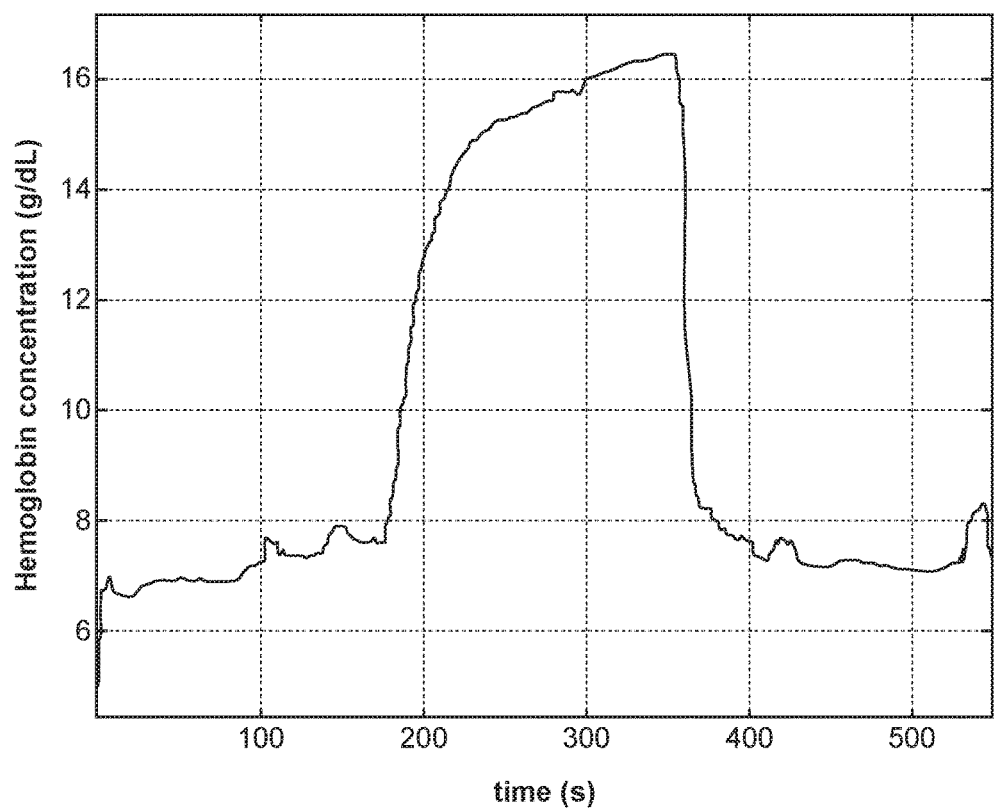
FIG. 12 is a plot illustrating an example of the projection method to calculate total hemoglobin concentration, according to an example of the present disclosure.

FIG. 12 illustrates an example of the projection method to calculate indices, as disclosed herein, being used to measure total hemoglobin. The optical-electronic device was applied to the arm of the user. Venous occlusion is applied to the user's arm at 176 seconds, resulting in a rapid increase in blood volume until 354 seconds, when the occlusion is removed and the blood volume is rapidly reduced.

Figure 13A:
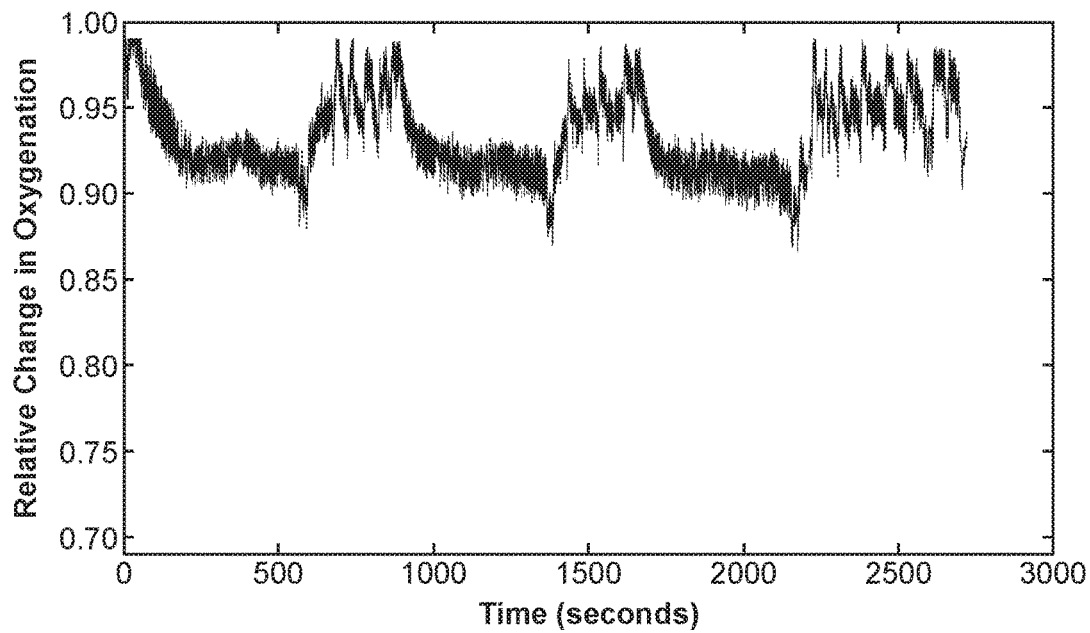
FIG. 13A is a plot corresponding to $SmO_2$ values calculated without using the A and B parameters determined using a lactate threshold (LT) assessment activity, according to an example of the present disclosure.
Figure 13B:
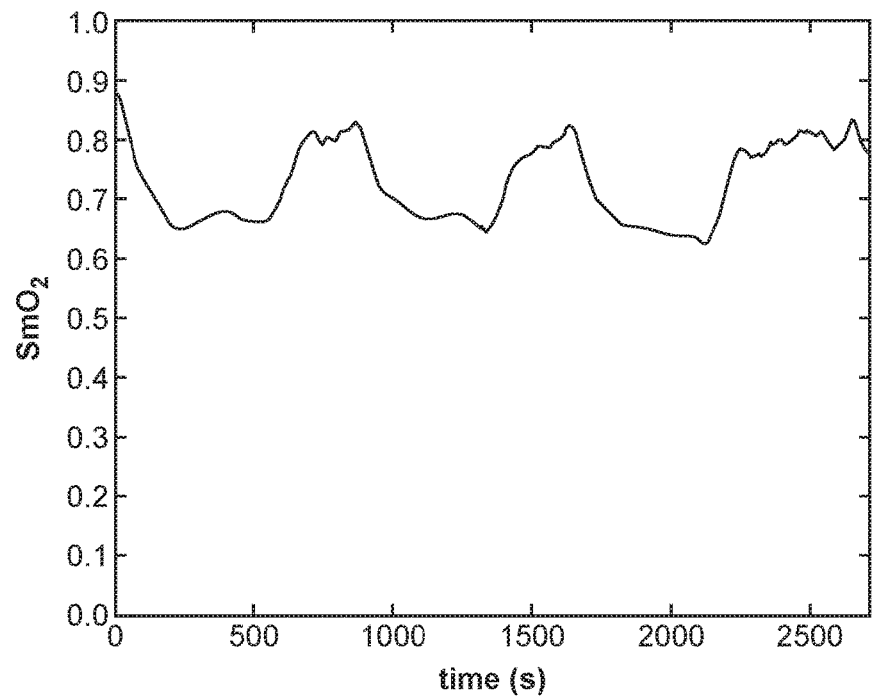
FIG. 13B is a plot showing $SmO_2$ data that was calculated using the A and B parameters according to the algorithm described in FIG. 8, according to an example of the present disclosure.

FIG. 13 shows the effect of determining user $SmO_2$ values adapted during an activity using the algorithm described in the flowchart presented in FIG. 8. FIG. 13A shows a plot corresponding to $SmO_2$ values calculated without using the A and B parameters determined using an LT assessment. FIG. 13B shows $SmO_2$ data that was calculated using the A and B parameters according to the algorithm described in FIG. 8, that shifts TOI down from a baseline of 100% and a range of 90-100% to a more user-specific baseline of 88% and a range of 65-88%.

Figure 14:
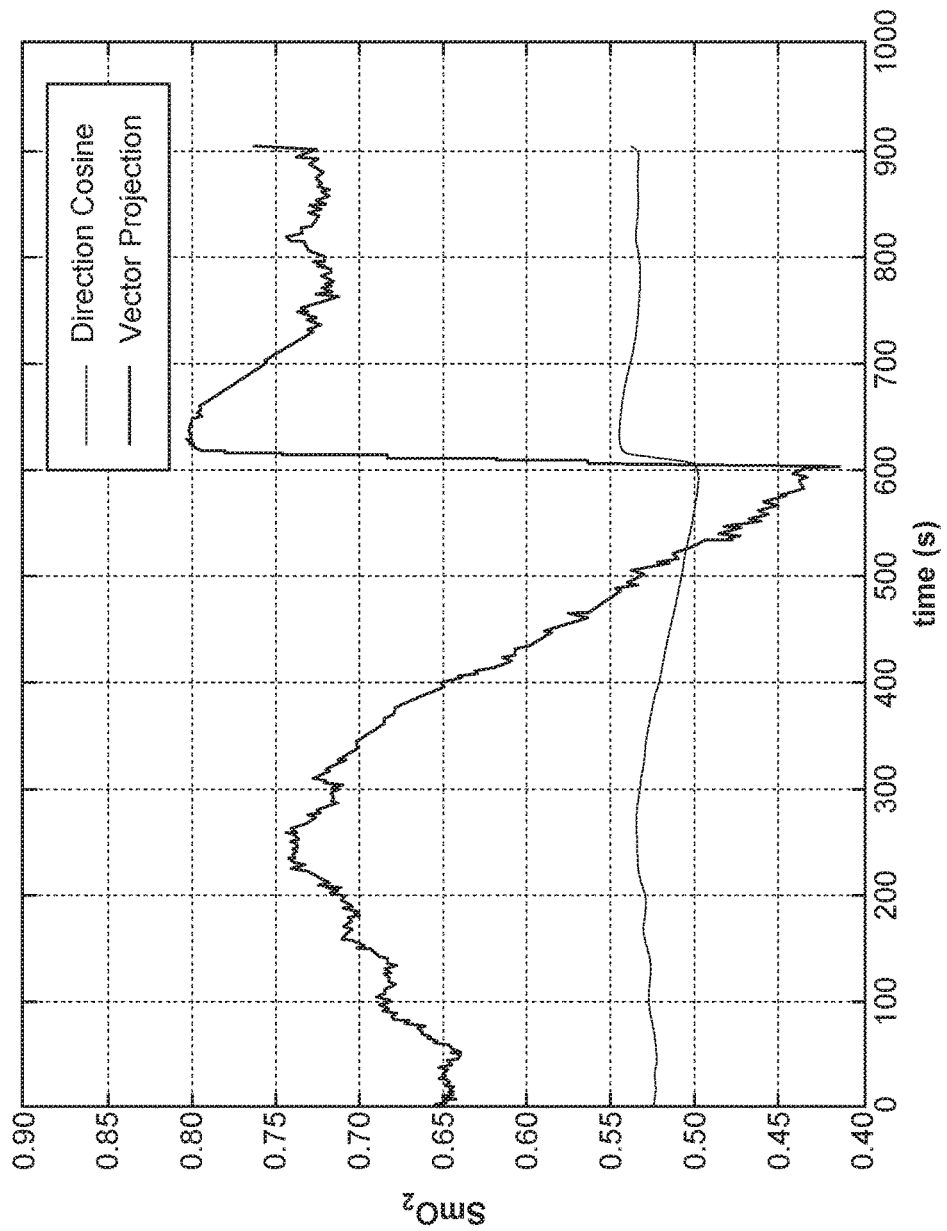
FIG. 14 is a plot comparing user $SmO_2$ values calculated according to a vector projection method (bottom) and a direction cosine method (top), according to an example of the present disclosure.

FIG. 14 compares user $SmO_2$ values calculated according to a direction cosine method (top) and a vector projection method (bottom).

Figure 15:
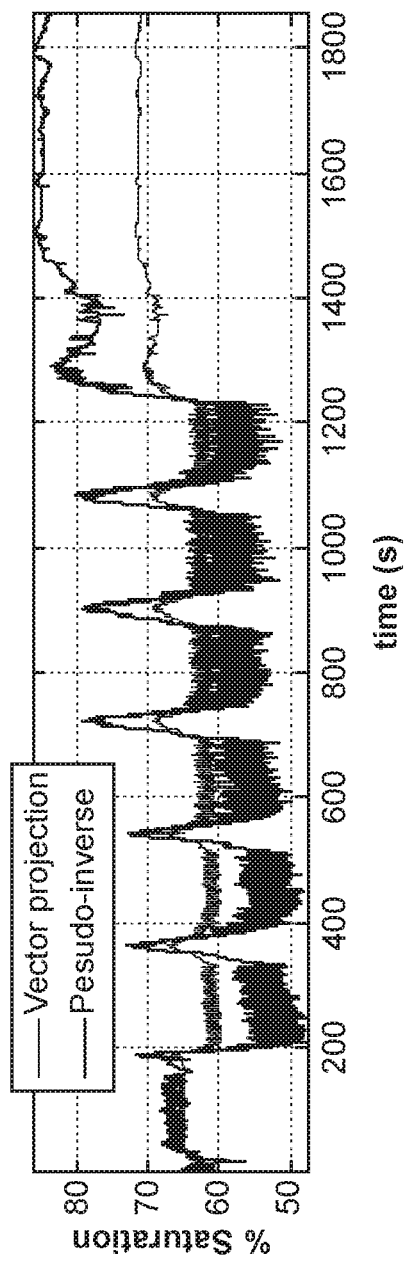
FIG. 15 is a plot comparing user Percentage (%) of Saturation $SmO_2$ values calculated according to a pseudo-inverse projection method (bottom) and a vector projection method (top), according to an example of the present disclosure.

FIG. 15 compares user Percentage (%) Saturation $SmO_2$ values calculated according to a pseudo-inverse projection method (bottom) and a vector projection method (top). The data was collected for a user wearing an optical-electronic device on their left calf while running an interval training session, consisting of running at a pace that increases every 180 s, with 30-second rest periods in between, giving rise to an increase in Percentage (%) of Saturation.

Figure 16A:
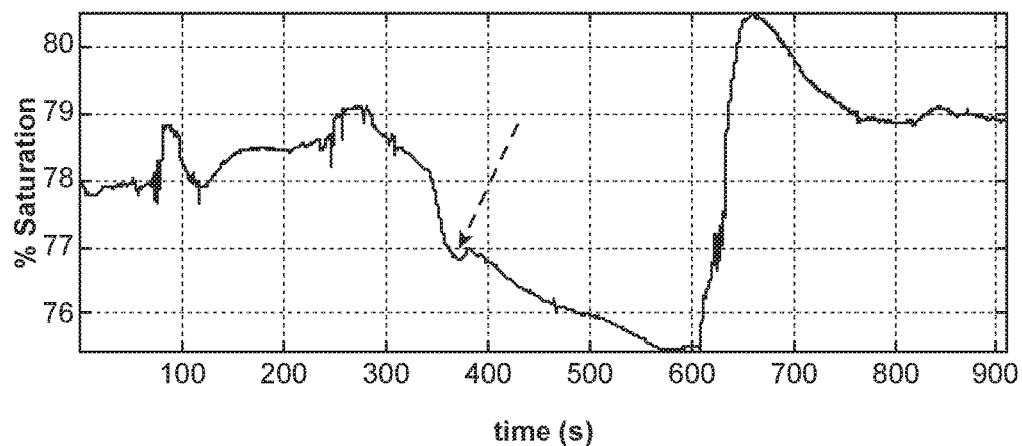
FIG. 16A is a plot demonstrating that the direct concentration method of calculating a biological indicator is affected by blood volume changes (dashed arrow) caused by arm occlusion, according to an example of the present disclosure.
Figure 16B:
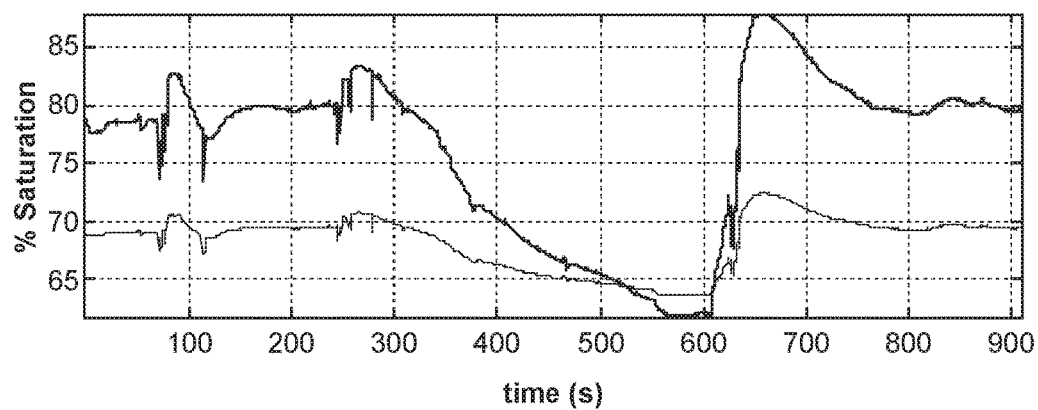
FIG. 16B is a plot demonstrating a smaller blood volume change dependence for the data calculated using the spectral projection methods, for both the vector projection method (bottom) and pseudo-inverse method (top), according to an example of the present disclosure.

FIG. 16 compares Percentage (%) of Saturation data collected during an arm occlusion test, calculated according to the spectral projection method (FIG. 16B) with a direct concentration measurement known in the art (FIG. 16A). As shown in FIG. 16A, the direct concentration method is affected by blood volume changes (dashed arrow) caused by arm occlusion. By contrast, FIG. 16B demonstrates a smaller blood volume change dependence for the data calculated using the spectral projection methods, for both the vector projection method (bottom) and pseudo-inverse method (top).

In addition to demonstrating less sensitivity to blood volume changes, the spectral projection method of determining biological indicator levels is also less affected by other confounding factors not directly related to chromophore tissue levels, including fat, melanin, scar tissue, tattoos, hair, and clothing. The spectral projection method is also less sensitive to factors that affect both paths of light equally, such as variations in temperature or ambient light. In the case of an optical-electronic device that includes two or more emitters and a single detector, the spectral projection method produces data that is less affected by variations in photodetector responsivity or trans-impedance amplifier gain. In the case of an optical-electronic device configured to include a single emitter and two or more photodetectors, the spectral projection method produces data that is less affected by variations in LED power and variations in spectrum.

The optical-electronic device, as disclosed herein, can also transmit a signal or an alert to an output device such as a user display or mobile device. One form of an alert can signal or flag the existence of extraneous factors which interfere with the identification and/or determination of one or more biological indicators. The existence of extraneous factors can be indicated by determining the relative match of a spectral data set representative of received light and the null space for a matrix containing the spectra representative of a predetermined data set of one or more chromophores, which is the set of vectors that will be mapped to 0 by the F matrix. As described at block 660 of FIG. 6, the inner product is calculated as $P_k=\Sigma_j\mu_a(j)Finv_{jk}$, where $P_k$ are the projections due to analyte k, and Finv is the pseudo-inverse of matrix F containing the spectra of the analytes at wavelengths j. The residual signal R is given by $R=|\mu_a-P*F^T|$, where T denotes the transpose, || denotes magnitude, and * denotes matrix multiplication. Accordingly, R represents the part of the detected signal that failed to project towards any of the analytes of interest. Under normal conditions, R remains low. However, under special conditions, such as when clothing interferes with the optical-electronic device, an abrupt increase in the modulus of R would be expected. When the modulus of R increases suddenly, or when it surpasses a pre-determined threshold, an alarm can be conveyed to the user. Accordingly, the optical-electronic device can be configured to generate a null-space or residual signal to flag the existence of extraneous factors, including, but not limited to: clothing, hair, tattoos, scar tissue, melanin, fat, poor sensor placement, and motion-related factors.

Figure 17A:
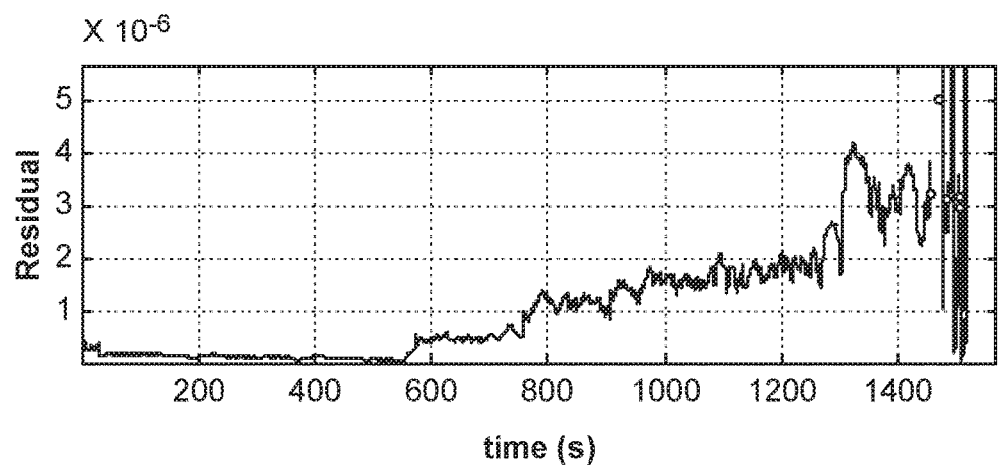
FIG. 17A is a plot illustrating an example of residual signal determination configured to detect interference over time, according to an example of the present disclosure.
Figure 17B:
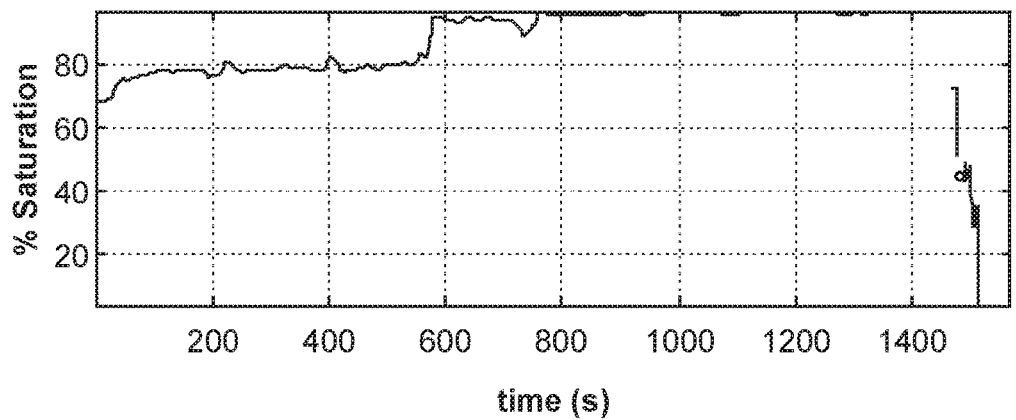
FIG. 17B is a plot illustrating Percentage of Saturation over time, where the time scale is the same as that of FIG. 17A.

FIG. 17A is a plot illustrating an example of residual signal determination configured to detect interference over time, according to an example of the present disclosure. FIG. 17B is a plot illustrating Percentage of Saturation over time, where the time scale is the same as that of FIG. 17A. FIGS. 17A and 17B illustrates an example of residual signal determination configured to detect interference. As shown in FIGS. 17A and 17B, the residual signal abruptly increased at 555 seconds indicating that the optical-electronic device monitored an unexpected signal. In this case, the abrupt change in residual signal was caused by sensor movement which in turn caused fabric to get in between one of the light emitters and the tissue being monitored.

Figure 18A:
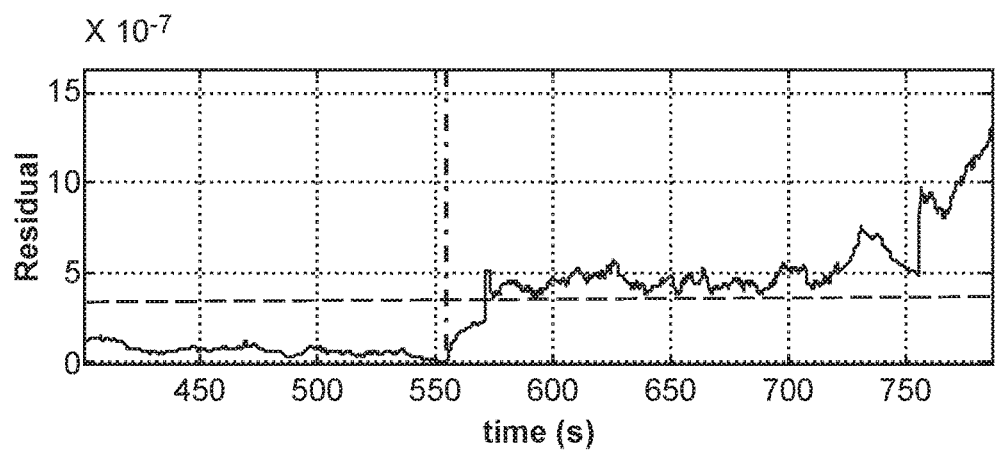
FIG. 18A is a plot illustrating a close-up view of the event at 555 seconds, shown in FIG. 17A, according to an example of the present disclosure.
Figure 18B:
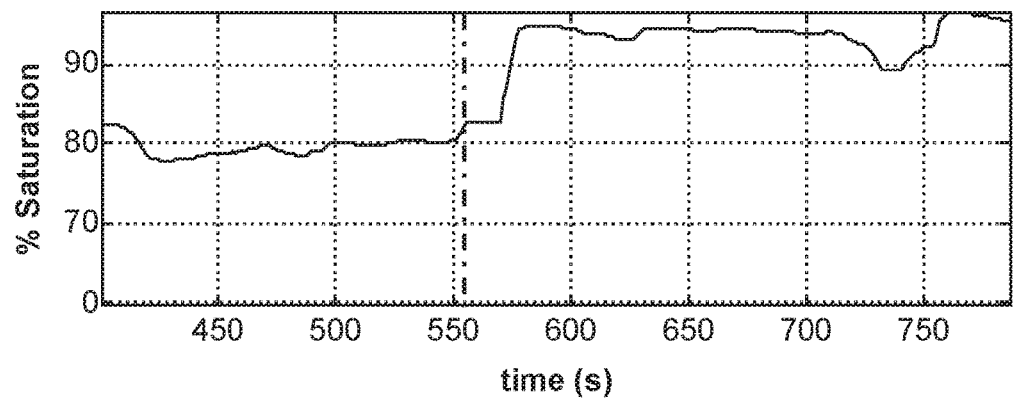
FIG. 18B is a plot illustrating Percentage of Saturation over time, where the time scale is the same as that of FIG. 18A.

FIG. 18A illustrates a close-up view of the event at 555 seconds, showing a clear and abrupt increase in the residual signal from FIG. 17A. FIG. 18B is a plot illustrating Percentage of Saturation over time, where the time scale is the same as that of FIG. 18A.

In this case, a threshold of about $4\times10^{-6}$ would provide the user with an alarm telling the user to check sensor placement, thereby increasing the reliability of the parameters being monitored by sensor and saving the user from the frustration of collecting invalid data.

The provision of an alert in response to an extraneous factor interfering the identification and determination of biological indicators is especially valuable to wearable athletic monitoring in which users move frequently using optical-electronic devices that can be interwoven in fabric and therefore increases the robustness of the optical-electronic device by providing a user with a clear indication of the occurrence of a problem.

Figure 19A:
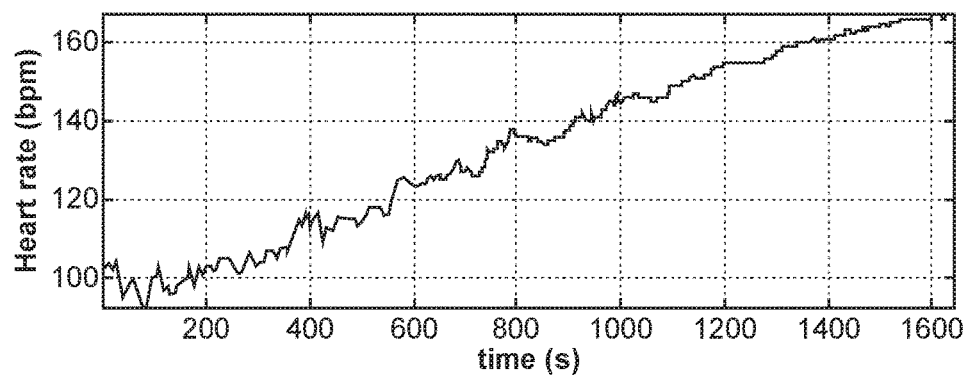
FIG. 19A is a plot illustrating the relative change in heart rate over time of a user during an assessment, according to an example of the present disclosure.
Figure 19B:
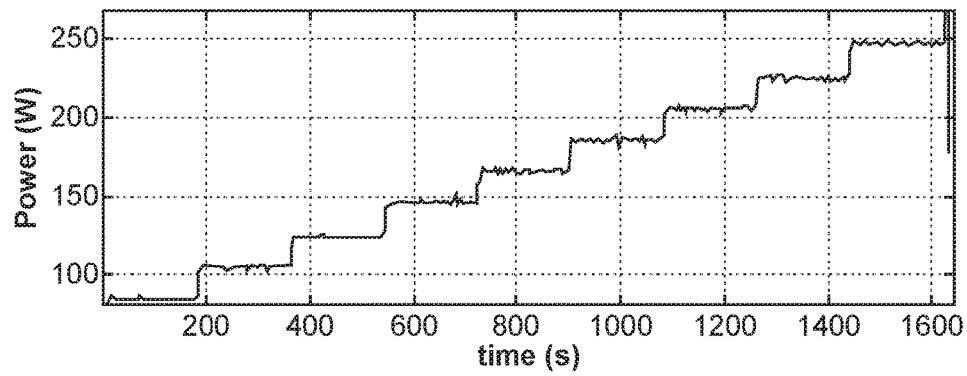
FIG. 19B is a plot illustrating the relative change in power output over time of a user during the assessment of FIG. 19A.
Figure 19C:
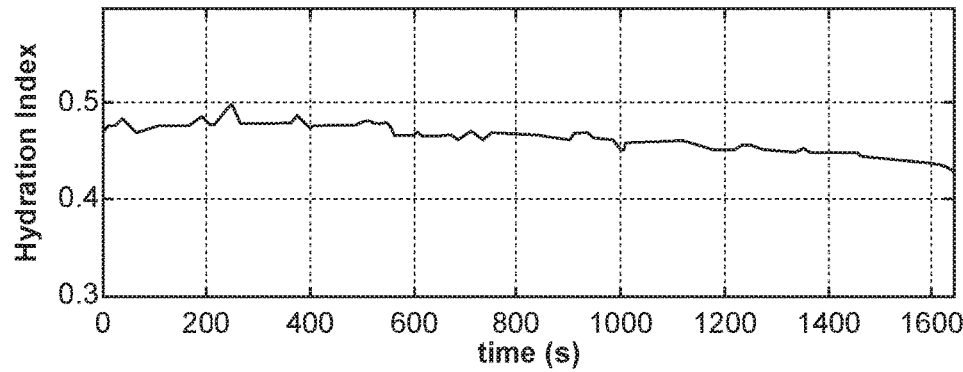
FIG. 19C is a plot illustrating the relative change in hydration index of a user during the assessment of FIG. 19A.

FIG. 19A is a plot illustrating the relative change in over time of a user during an assessment, according to an example of the present disclosure. FIG. 19B is a plot illustrating the relative change in power output over time of a user during the assessment of FIG. 19A. FIG. 19C is a plot illustrating the relative change in hydration index of a user during the assessment of FIG. 19A. As shown in FIGS. 19A-C, as the time and exertion level increases over the course of the assessment protocol, the hydration level decreases, as would be expected due to increased diaphoresis and respiration. This is especially true close to the end of the assessment, when exertion levels are the highest.

Figure 20A:
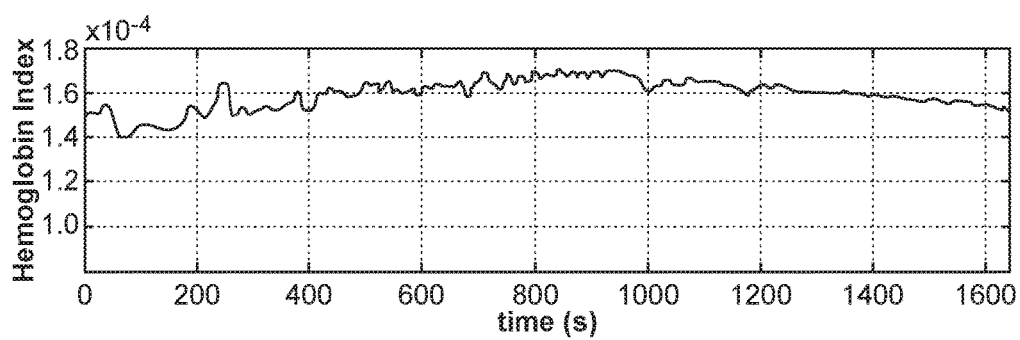
FIG. 20A is a plot illustrating the relative change in hemoglobin index during the same assessment shown in FIG. 19A.
Figure 20B:
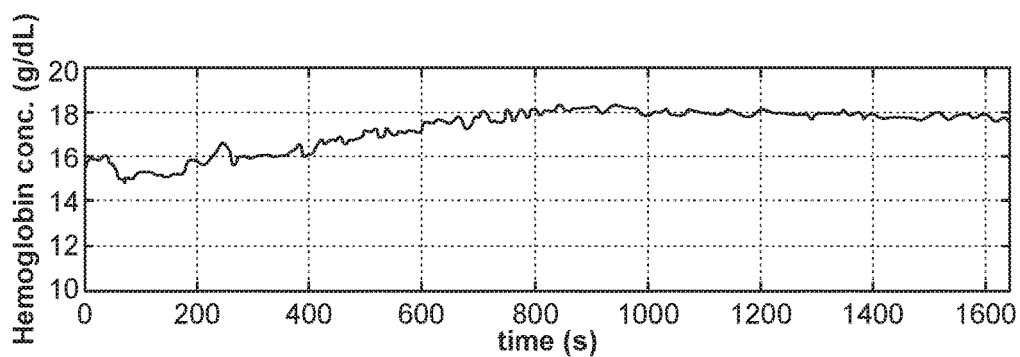
FIG. 20B is a plot illustrating the relative change in hemoglobin concentration during the same assessment shown in FIG. 19A.

FIG. 20A is a plot illustrating the relative change in hemoglobin index during the same assessment shown in FIGS. 19A-C. FIG. 20B is a plot illustrating the relative change in hemoglobin concentration during the same assessment shown in FIGS. 19A-C. The change in total hemoglobin shown in FIG. 20B was calculated according to the pseudo-inverse projection method. FIGS. 20A-B also shows that as more hemoglobin becomes present in the capillaries of the muscle being monitored, the gastrocnemius muscle in this case, the higher the total hemoglobin detected by the optical-electronic device.

As shown in FIGS. 20A-B, as the user approaches exhaustion, the total hemoglobin level starts to drop with a reduction in the level of hydration. The hemoglobin concentration, on the other hand, remains fairly constant after reaching a peak level around 800 seconds. The hemoglobin concentration plot can be generated by taking the ratio between the total hemoglobin index and the relative hydration and multiplying by a user-specific proportionality constant.

As shown in FIGS. 20A-B, the perfusion characteristics of muscle, including blood volume, pulsatile rhythm, vascular tone, muscular tone, and angiogenesis, can be monitored during an assessment by determining total hemoglobin and hydration using the optical-electronic device.

In addition to the generation of an alarm or alert for non-biological interference, the magnitude of the residual can be an indicator of biological interference. The residual can represent a real physiological signal due to a change in one or more chromophores not quantified by the projection onto the known list of chromophores. The set of vectors corresponding to the null space of F can be used to postulate the existence of another set of chromophores in the tissues being monitored. Further, the null space set of vectors can be used as a starting point for determining the identity of additional chromophores that can be monitored.

Figure 21A:
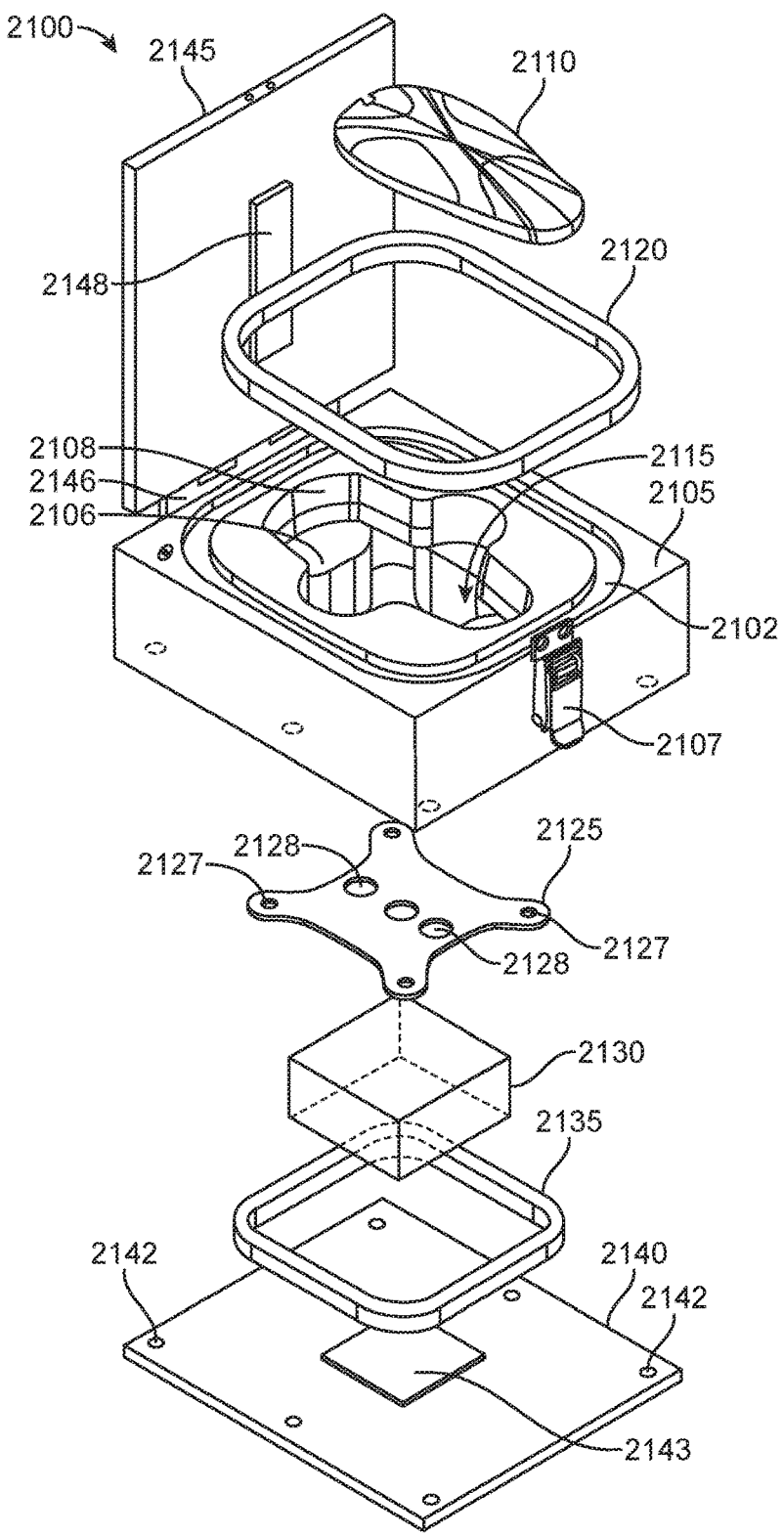
FIG. 21A is an exploded view of a calibration container, according to an example of the present disclosure.

According to at least one example of the present disclosure, the presently disclosed optical-electronic device can be calibrated using a calibration container, such as that shown in FIGS. 21A-D. FIG. 21A provides an exploded view of an example calibration container 2100 that is suitable for use in calibrating an electronic device 2110, such as, for example, any of the optical-electronic devices described in the present disclosure. For example, the calibration methods described with respect to FIGS. 5A and 5B can, at least in some instances, be conducted using one or more calibration containers, such as the calibration container shown in FIG. 21.

As depicted in FIG. 21A, the calibration container 2100 can include a main body 2105 forming a through opening 2115 configured to receive an object having known optical properties 2130 on one side and an electronic device 2110 on another side. The main body 2105, as well as other portions of the calibration container 2100, may comprise any suitable material that is opaque to light, including, but not limited to, Black DELRIN® (a type of polyoxymethylene) or black-anodized aluminum. Additionally, the main body can be configured to block and absorb light. In at least one example, a film can cover the main body to assist in the blocking and absorption of light. In at least some instances, the object having known optical properties 2130 can be a phantom or an object having a known optical density such as that described with respect to FIGS. 5A and 5B. The calibration container 2100 serves to contain the electronic device 2110 and the object having known optical properties 2130 securely together in a stable and light-tight environment. In one example, the object can be included with the calibration container 2100. In another example, the object can be purchased separately or obtained from another source.

As depicted in FIG. 21A, the main body 2105 forms a first support ledge 2106 and a second support ledge 2108 configured to support the electronic device 2110 on a first side and a second side. The electronic device 2110 is configured to emit light from a plurality of emitters and receive light at a detector. In at least some instances, the electronic device 2110 is a spatially-resolved light-emitting device.

The calibration container 2100 can include an upper lid 2145 coupled with the main body 2105 and configured to securely enclose one side of the main body 2105. The upper lid 2145 is used to close the calibration container 2100 during calibration to prevent light from interfering with the calibration measurements and method. The calibration container 2100 can further include, in at least some instances, a hinge 2146 configured to couple the upper lid 2145 to the main body 2105. The calibration container 2100 can also include a latch 2107 configured to releasably secure the upper lid 2145 to the main body 2105. The latch 2107 also facilitates insertion and removal of the electronic device 2110 from the calibration container 2100 and can in some instances provide for a more consistent positioning between the electronic device 2110 and the object having known optical properties 2130.

The calibration container 2100 can further include a first gasket 2120 configured to be mounted between the main body 2105 and the upper lid 2145. As depicted in FIG. 21A, the main body 2105 forms a first gasket groove 2102 configured to receive a portion of the first gasket 2120. The first gasket 2120 can help provide firm closure of the upper lid 2145 to the main body 2105 while maintaining a light-tight seal during calibration of the electronic device 2110. In at least some instances, the calibration container 2100 can include an upper elastic material 2148 coupled with the upper lid 2145. The upper elastic material 2148 can be configured to hold the electronic device 2110 in place against the first support ledge 2106 and the second support ledge 2108. The upper elastic material 2148 can be configured, at least in some instances, to gently push the device down during the closing of upper lid 2145 to facilitate correct positioning and alignment of the electronic device 2110 during calibration.

As depicted in FIG. 21A, the calibration container 2100 can further include a lower lid 2140 coupled to the main body 2105 and configured to securely enclose the other side of the main body 2105. The lower lid 2140 is coupled with the object having known optical properties 2130 and encloses the object having known optical properties 2130 into a portion of the main body 2105, configured to receive the object having known optical properties 2130. In at least some instances, the lower lid 2140 is coupled to the main body 2105 by a plurality of threaded connections 2142, thereby securing the object having known optical properties 2130 within the main body 2105.

As depicted in FIG. 21A, the calibration container 2100 can also include a second gasket 2135 configured to be mounted between the main body 2105 and the lower lid 2140. In at least some instances, the main body 2105 can form a second gasket groove configured to receive a portion of the second gasket. The second gasket 2135 forms a light-tight seal between the lower lid 2140 and the main body 2105 after the lower lid 2140 is secured to the main body 2105. The calibration container 2100 can further include a support plate 2125 configured to hold the electronic device 2110 in close proximity to the object having known optical properties 2130. The support plate 2125 can comprise any suitable material, including, but not limited to, Black Black DELRIN® or anodized aluminum. In at least some instances, the support plate 2125 forms at least three through holes 2128 corresponding to locations of the plurality of emitters and the detector on the electronic device 2110. The through holes 2128 defines the apertures through which light can propagate out from emitters on the electronic device 2110 toward and through the object with known optical properties 2130. The through holes 2128 also define the aperture through which light can propagate toward a detector on the electronic device 2110 from the object with known optical properties 2130. In some instances, the support plate 2125 can be coupled to the main body 2105 by a plurality of threaded connections 2127.

In at least some instances, the calibration container 2100 can include a lower elastic material 2143 coupled to the lower lid 2140. The lower elastic material 2143 can be configured to press the object having known optical properties 2130 against the support plate. In at least some instances, the lower elastic material 2143 facilitates correct positioning and alignment of the object having known optical properties 2130 in the main body 2105 during calibration of the electronic device 2110.

Figure 21B:
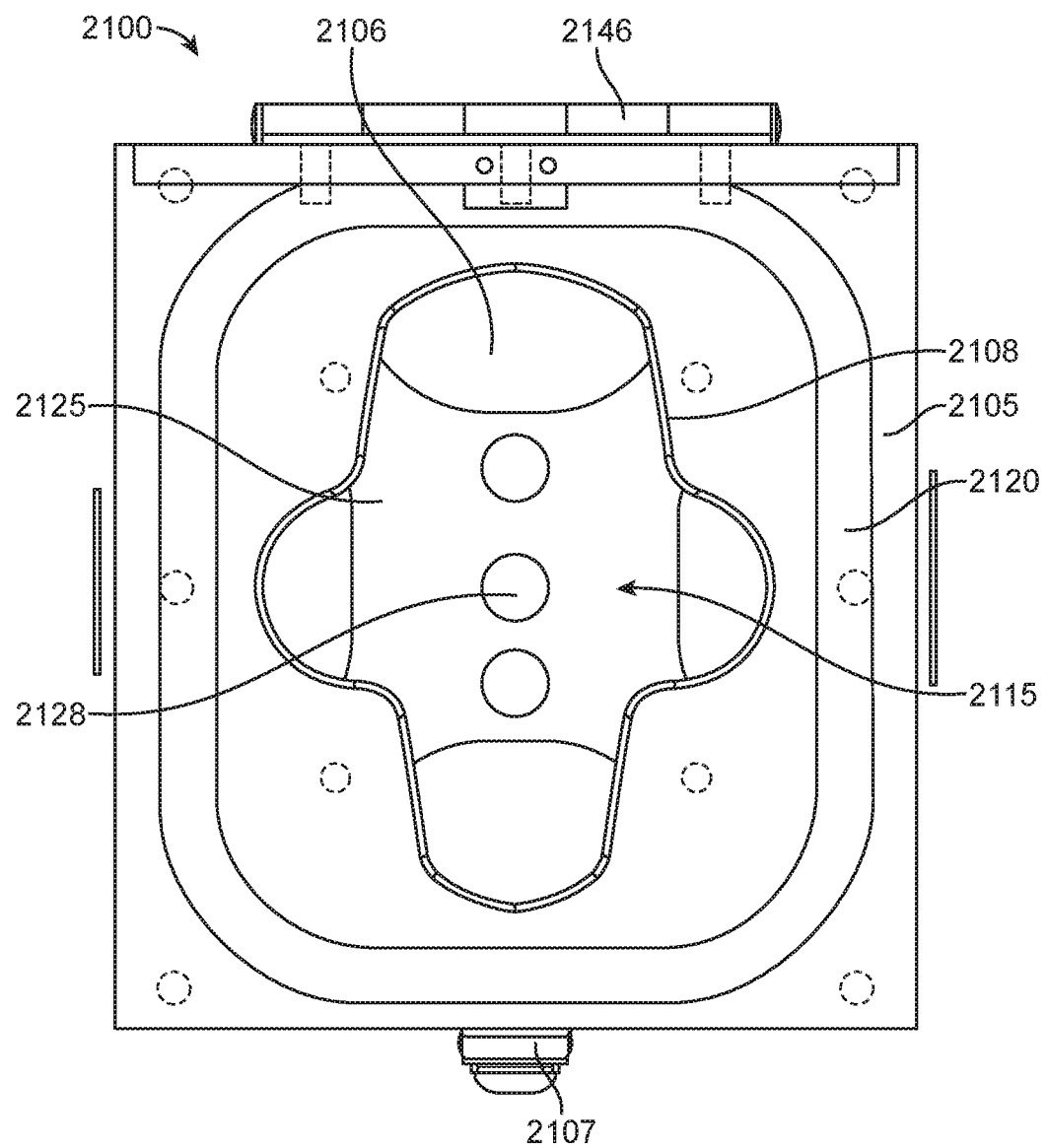
FIG. 21B is a top perspective view of an interior portion of a calibration container, according to an example of the present disclosure.

FIG. 21B is a top perspective view of an interior portion of the calibration container 2100 shown in FIG. 21A. FIG. 21B depicts the calibration container 2100 with the upper lid 2145 open thereby showing main body 2105 forming a through opening 2115 configured to receive an electronic device 2110. The main body 2105 further forms a first support ledge 2106 and a second support ledge 2108 configured to support the electronic device 2110 on a first side and a second side. The calibration container 2100 also includes a first gasket 2120 mounted on the main body 2105 configured to provide firm closure of the upper lid 2145 to the main body 2105 while maintaining a light-tight seal during calibration of the electronic device 2110. FIG. 21B also shows support plate 2125 having three through holes 2128 corresponding to locations of the plurality of emitters and the detector on the electronic device 2110. While three through holes 2128 are illustrated, the number of through holes 2128 can vary. As illustrated, each of the through holes 2128 correspond to one of the emitters or detector. In other examples, a through hole 2128 can serve one or more emitters or detectors. The through holes 2128 allows light from emitters on the electronic device 2110 to propagate toward and through the object with known optical properties 2130.

Figure 21C:
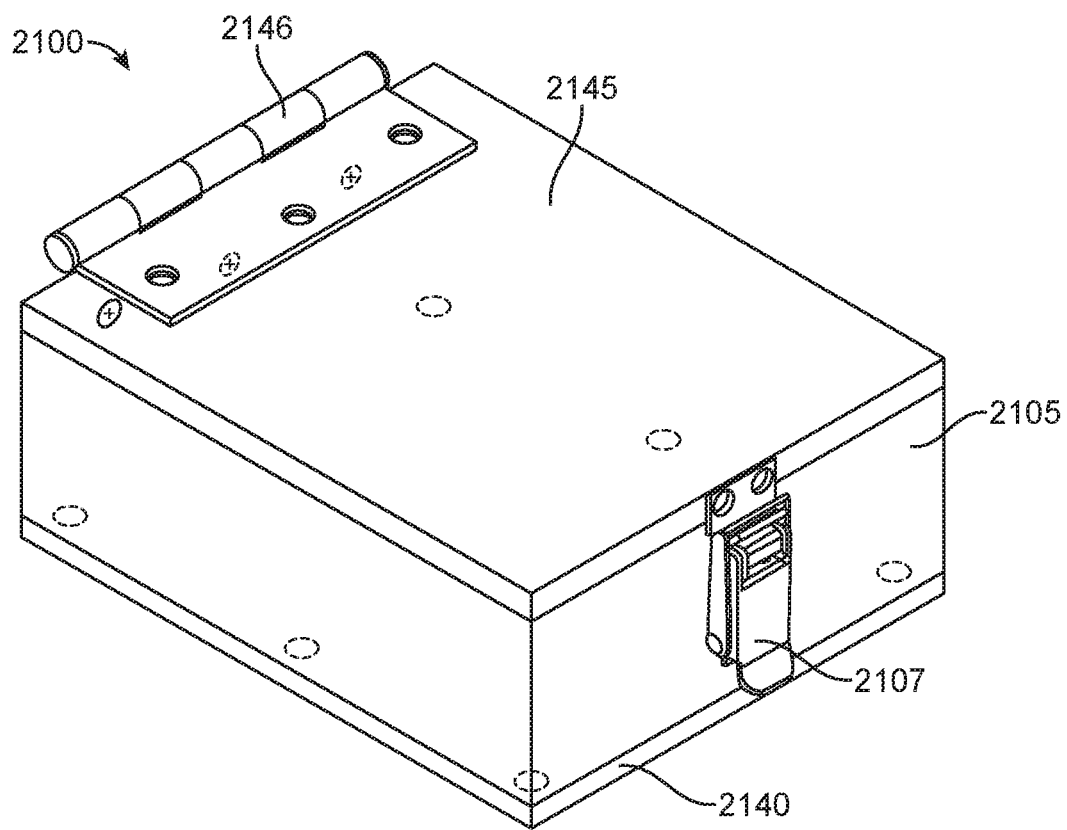
FIG. 21C is a perspective view of exterior portions of a calibration container, according to an example of the present disclosure.

FIG. 21C is a perspective view of the calibration container 2100 with the upper lid 2145 closed to securely enclose the electronic device 2110 and object having known optical properties 2130 inside the main body 2105. The upper lid 2145 is used to close the calibration container 2100 during calibration to prevent light from interfering with the calibration measurements and method.

FIG. 21D is a cross-sectional view of the calibration container 2100 showing the electronic device 2110 secured in the main body 2105 between the upper lid 2145 and calibration block 2130. The support plate 2125 provides through holes corresponding to the emitters and detector on the electronic device 2110.

The examples shown and described above are only examples. Even though numerous characteristics and advantages of the present technology have been set forth in the foregoing description, together with details of the structure and function of the present disclosure, the disclosure is illustrative only, and changes can be made in the detail, including in matters of shape, size and arrangement of the parts within the principles of the present disclosure, up to, and including, the full extent established by the broad general meaning of the terms used in the claims.

What is claimed is:

1. A device configured to generate at least one calibration factor for use in determining optical density, the device comprising:
    a plurality of emitters, each having at least one light source, each of the emitters configured to emit light;
    a detector configured to receive light and transmit data representative of the received light;
    at least two of the plurality of emitters are spaced at different distances from the detector;
    a processor coupled to the at least one emitter and the detector;
    a non-transitory storage medium coupled to the processor and configured to store instructions to cause the device to repeat the following for each of the light sources:
        emit light from one of the light sources of one of the emitters at a predetermined current towards an object that has a known optical density;
        detect, at the detector, a portion of the emitted light corresponding to the predetermined current;
        calculate, at the processor, a corresponding calibration factor based on the detected portion of emitted light through the object;
        store the corresponding calibration factor in the non-transitory storage medium.

2. The device as recited in claim 1, further comprising instructions to cause, repeatedly for each light source and each of a plurality of predetermined currents, the device to:
    emit light from one of the at least one light source of the at least one emitter at one of the plurality of predetermined currents towards the object;
    detect, at the detector, a portion of the emitted light corresponding to the predetermined current;
    calculate, at the processor, a corresponding calibration factor based on the detected portion of emitted light through the object;
    store the corresponding calibration factor in the non-transitory storage medium.

3. The device as recited in claim 1, wherein the at least one emitter comprises a plurality of emitters and each of the plurality of emitters having a plurality of light sources, and further comprising instructions to cause the device to:

emit light, towards the object, from one of the plurality of light sources of one of the emitters at one of a plurality of predetermined currents;

detect, at the detector, a portion of the emitted light corresponding to the one of a the plurality of predetermined currents;

calculate, at the processor, a corresponding calibration factor based on the detected portion of emitted light through the object;

store the corresponding calibration factor in the non-transitory storage medium.

4. The device as recited in claim 1, wherein the predetermined current comprises a plurality of currents and each of the steps are performed for each of the plurality of currents.

5. The device in claim 4, further comprising instructions stored on the non-transitory storage medium to cause the device to:

confirm that at least one calibration factor is stored for each light source at the plurality of currents.

6. The device as recited in claim 5, wherein the plurality of predetermined currents are based on a corresponding plurality of predetermined currents and the calculation of the corresponding calibration factor is derived using the formula: $C_{ijm}=10^{OD_{jm}}/D_{ijm}$, where i is an index tracking a predetermined current value, j is an index tracking a light source, m is an index tracking a spacing between the light source and detector, OD is the optical density, and D is measured light data.

7. The device as recited in claim 5, wherein the non-transitory storage medium further comprises instructions, upon receiving a measurement command, to:

emitting, iteratively, light from one of a plurality of light sources at one of a plurality of predetermined currents towards the object;

detecting, at a detector, a portion of the emitted light corresponding to a respective one of the light sources and predetermined currents;

determining an optical density of the object based on the calibration factors.

8. The device as recited in claim 1, wherein the corresponding calibration factor is transmitted via a network interface component to a server.

9. The device as recited in claim 1, wherein the corresponding calibration factor is transmitted via a network interface component to an external electronic device.

10. The device as recited in claim 1, wherein the object is made of a material that is designed to mimic a biological tissue.

11. The device as recited in claim 1, wherein the at least one emitter comprises at least two emitters that are spaced apart from each other and from the detector.

12. The device as recited in claim 11, wherein one of the emitters is further away from the detector than the other.

13. The device as recited in claim 12, wherein each of the emitters are arranged along a ray extending from the detector.

14. The device as recited in claim 12, wherein each of the emitters are located on a same side of the detector.

15. The device as recited in claim 11, wherein each of the two emitters comprise a plurality of light sources.

16. The device as recited in claim 15, wherein each of the two emitters comprise four light sources.

17. The device as recited in claim 15, wherein each of the plurality of light sources within a given one of the at least two emitters has a different peak wavelength of emission.

18. A system including an electronic device and a hardware server, the system configured to generate at least one calibration factor for use in determining optical density and comprising:

a plurality of emitters, each having at least one light source, each of the emitters configured to emit light;

a detector configured to receive light and transmit data representative of the received light;

at least two of the plurality of emitters are spaced at different distances from the detector;

a processor coupled to the at least one emitter and the detector;

a non-transitory storage medium coupled to the processor and configured to store instructions to cause the device to repeat the following for each of the light sources:

emit light from one of the light sources of one of the emitters at a predetermined current towards an object that has a known optical density;

detect, at the detector, a portion of the emitted light corresponding to the predetermined current;

calculate, at the processor, a corresponding calibration factor based on the detected portion of emitted light through the object;

store the corresponding calibration factor in the non-transitory storage medium.

* * * * *